United States Patent [19]

Nugent

[11] Patent Number: 5,412,141
[45] Date of Patent: May 2, 1995

[54] BISPHOSPHONIC ACID DERIVATIVES AS ANTI-ARTHRITIC AGENTS

[75] Inventor: Richard A. Nugent, Galesburg, Mich.

[73] Assignee: The Upjohn Company, Kalamazoo, Mich.

[21] Appl. No.: 19,964

[22] Filed: Feb. 19, 1993

Related U.S. Application Data

[63] Continuation-in-part of Ser. No. 570,274, Aug. 21, 1990, abandoned.

[51] Int. Cl.$^6$ .............. C07C 67/30; C07F 9/40; C07F 9/44; C07F 9/58
[52] U.S. Cl. .............. 558/214; 562/8; 546/22; 546/23; 548/112; 548/113; 548/128; 549/5; 549/6
[58] Field of Search .............. 562/8; 558/214

[56] References Cited

U.S. PATENT DOCUMENTS

| | | | |
|---|---|---|---|
| 3,683,080 | 8/1972 | Francis | 514/107 |
| 4,312,875 | 1/1982 | Lesher et al. | 514/332 |
| 4,746,654 | 5/1988 | Breliere et al. | 514/108 |

FOREIGN PATENT DOCUMENTS

| | | | |
|---|---|---|---|
| 51534/85 | 6/1986 | Australia | 546/22 |
| 0347027 | 12/1989 | European Pat. Off. | 546/288 |
| 2470124 | 5/1981 | France | 514/332 |
| WO88/06158 | 8/1988 | France | 544/243 |
| 2637477 | 2/1978 | Germany | 546/270 |
| 3719513A | 6/1987 | Germany | 540/468 |
| 63-295595A | 10/1986 | Japan | 546/22 |
| 63-185993A | 8/1988 | Japan | 546/22 |
| 8400756 | 3/1984 | WIPO | 514/314 |

OTHER PUBLICATIONS

Surtz, G. et al., *Synthesis*, "Synthesis of Novel Functionalized *gem*-Bisphosphonates," 661–662 (1991).
V. H. Wissman et al., Angew. Chemie 1980, 92(2), 129–130.
Helvetica Chimica Acta. vol. XLI, (1958)-No. 66, pp. 539–547.
J. Org. Chem. 1980, 45, "Photochemical Syntheses of 1,2-Diazepines. 11.1 Regiospecific Synthesis of 1,2-Dihydro-1,2-diazepin-3-ones", pp. 5095–5100.

*Primary Examiner*—Alan L. Rotman
*Attorney, Agent, or Firm*—Bruce Stein

[57] ABSTRACT

The bisphosphonates of formula (III)

$$R_2-X-(CW)_{m1}-CR_3R_4-CH_2-CM-[PO-(OR_1)_2]_2 \quad (III)$$

bicyclic bisphosphonates (V), and cyclic bisphosphonates (VII) are useful as anti-arthritic agents and do not have the side effects of anti-arthritic agents which are prostaglandin synthetase inhibitors.

8 Claims, No Drawings

BISPHOSPHONIC ACID DERIVATIVES AS ANTI-ARTHRITIC AGENTS

CROSS-REFERENCE TO RELATED APPLICATIONS

The present patent application is a continuation (national phase) application of PCT application PCT/U.S. No. 91/05554, filed Aug. 9, 1991, which is a continuation-in-part of U.S. application Ser. No. 07/570,274, filed Aug. 21, 1990, now abandoned.

BACKGROUND OF THE INVENTION

1. Field of the Invention

The invention is bisphosphonic acids, their esters and pharmaceutically acceptable salts which are useful as anti-arthritic agents.

2. Description of the Related Art

U.S. Pat. No. 4,746,654 discloses bisphosphonates useful as anti-inflammatory agents.

Australian Patent A-5 1534/85 discloses bisphosphonates useful in treating abnormal calcium and phosphorous metabolism and useful in treating arthritis.

U.S. Pat. No. 3,683,080 discloses polyphosphonates, in particular diphosphonates useful in inhibiting anomalous deposition and mobilization of calcium phosphate in animal tissue.

DE 3,719,513-A (Derwent 89-000580/01) discloses diphosphonic acid derivatives useful in treatment of disorders of calcium metabolism.

WO88/06158 discloses the reaction of activated methylenes with vinylidene diphosphonates.

International Publication Number WO90/12017 for International Application Number PCT/U.S. No. 90/01106 discloses geminal bisphosphonic acids and derivatives thereof as anti-arthritic agents.

J6 3185-993-A discloses ethanones and J6 3295-595-A discloses propanones similar to the 4,4-diphosphonic acid (ester)-1-butanones of the present invention.

Synthesis, 661 (August, 1991) discloses the compound of EXAMPLE 47 of the present invention in its compound 3e.

The present invention is to compounds which while anti-arthritic are not prostaglandin synthetase inhibitors which is an advantage in that the side effects of the prostaglandin synthetase inhibitor anti-arthritic compounds are eliminated.

SUMMARY OF INVENTION

Disclosed are acyclic bisphosphonates of formula (III)

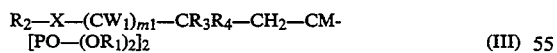

(III)

where
$m_1$ is 0 or 1;
M is —H, —Cl or —CH$_3$;
$R_1$ are the same or different and are selected from the group consisting of —H, C$_1$-C$_6$ alkyl, —CH$_2$—$\phi$, —$\phi$ optionally substituted with 1 thru 5 —NO$_2$, —F, —Cl, —Br, —I or C$_1$-C$_4$ alkyl, and where both —OR$_1$ on the same P are taken together along with —CH$_2$—CH$_2$—, —CH$_2$—CH$_2$—CH$_2$— or —CH$_2$—C(CH$_3$)$_2$—CH$_2$— to form a heterocyclic ring containing one —P—, two —O— and two or three carbon atoms;

$R_2$ is (1)—$\phi$ optionally substituted with 1 or 2 —$\phi$ or with 1 thru 5 —F, —Cl, —Br, —I, —NO$_2$, —CN, —CF$_3$, C$_1$-C$_{10}$ alkyl, C$_3$-C$_7$ cycloalkyl, —OH, C$_1$-C$_4$ alkoxy, —SH, —NH$_2$, —O—CO—R$_{2\text{-}1}$ where R$_{2\text{-}1}$ is
C$_1$-C$_{10}$ alkyl,
C$_3$-C$_7$ cycloalkyl,
pyridine,
—(CH$_2$)$_{n1}$—COO—R$_{2\text{-}2}$ where $n_1$ is 1 thru 3 and R$_{2\text{-}2}$ is
—H,
C$_1$-C$_6$ alkyl,
—$\phi$,
—CH$_2$—$\phi$,
—$\phi$ optionally substituted with 1 thru 3, —F, —Cl, —Br, —I, —NO$_2$, —CN, —CF$_3$, C$_1$-C$_{10}$ alkyl, C$_3$-C$_7$ cycloalkyl, —OH, C$_1$-C$_4$ alkoxy, —O—$\phi$, C$_1$-C$_4$ alkylthio, —N—CO—R$_{2\text{-}3}$ where R$_{2\text{-}3}$ is C$_1$-C$_{10}$ alkyl,
C$_3$-C$_7$ cycloalkyl,
pyridine,
—(CH$_2$)$_{n4}$—COO—R$_{2\text{-}9}$ where $n_4$ is 1 thru 3 and R$_{2\text{-}9}$ is —H,
C$_1$-C$_6$ alkyl,
—$\phi$,
—CH$_2$—$\phi$,
—$\phi$ optionally substituted with 1 thru 3 —F, —Cl, —Br, —I, —NO$_2$, —CN, —CF$_3$, C$_1$-C$_{10}$ alkyl, C$_3$-C$_7$ cycloalkyl, —OH, C$_1$-C$_4$ alkoxy, —O—$\phi$, C$_1$-C$_4$ alkylthio,
—O—S(O)$_2$—R$_{2\text{-}4}$ where R$_{2\text{-}4}$ is
C$_1$-C$_{10}$ alkyl,
—$\phi$ optionally substituted with 1 thru 3 —F, —Cl, —Br, —I, —NO$_2$, —CN, —CF$_3$, C$_1$-C$_{10}$ alkyl, C$_3$-C$_7$ cycloalkyl, —OH, C$_1$-C$_4$ alkoxy, —O—$\phi$, C$_1$-C$_4$ alkylthio, —N—CO—R$_{2\text{-}3}$ where R$_{2\text{-}3}$ is as defined above,
naphthalene optionally substituted with 1 or 2 —$\phi$,
naphthalene optionally substituted with 1-7 —F, —Cl, —Br, —I, —NO$_2$, —CN, —CF$_3$, C$_1$-C$_{10}$ alkyl, C$_3$-C$_7$ cycloalkyl, —OH, C$_1$-C$_4$ alkoxy, —O—$\phi$, C$_1$-C$_4$ alkylthio or —N(CH$_3$)$_2$, —N(R$_{2\text{-}5}$)(R$_{2\text{-}6}$) where R$_{2\text{-}5}$ and R$_{2\text{-}6}$ are the same or different and are —H, C$_1$-C$_6$ alkyl, C$_3$-C$_7$ cycloalkyl, —$\phi$, 2-pyridinyl, 3-pyridinyl, 4-pyridinyl, and where R$_{2\text{-}5}$ and R$_{2\text{-}6}$ are taken together with the attached nitrogen atom to form a heterocyclic ring containing 4 thru 6 carbon atoms, a 1-morpholine and 1-piperidine ring,
—N(R$_{2\text{-}7}$)—CO—R$_{2\text{-}1}$ where R$_{2\text{-}7}$ is H, C$_1$-C$_6$ alkyl, C$_3$-C$_7$ cycloalkyl, —$\phi$, 2-pyridinyl, 3-pyridinyl, 4-pyridinyl, and where R$_{2\text{-}1}$ is as defined above,
—N(R$_{2\text{-}5}$)—CO—O—R$_{2\text{-}8}$ where R$_{2\text{-}8}$ is —H, C$_1$-C$_6$ alkyl, C$_3$-C$_7$ cycloalkyl, —$\phi$ and —CH$_2$—$\phi$,
—N(R$_{2\text{-}7}$)—CO—N(R$_{2\text{-}5}$)(R$_{2\text{-}6}$) where R$_{2\text{-}5}$, R$_{2\text{-}6}$ and R$_{2\text{-}7}$ are as defined above,
—N(R$_{2\text{-}7}$)—SO$_2$—R$_{2\text{-}4}$ where R$_{2\text{-}4}$ and R$_{2\text{-}7}$ are as defined above, (2) 2- and 3-furanyl optionally substituted with 1 or 2 —$\phi$, or with 1 thru 3 —F, —Cl, —Br, —I, —NO$_2$, —CN, —CF$_3$, C$_1$-C$_{10}$ alkyl, C$_3$-C$_7$ cycloalkyl, —OH, —SH, —NH$_2$,
—O—CO—R$_{2\text{-}1}$ where R$_{2\text{-}1}$ is as defined above, —O—S(O)$_2$—R$_{2-4}$ where R$_{2-4}$ is as defined above,
—N(R$_{2-5}$)(R$_{2-6}$) where R$_{2-5}$ and R$_{2-6}$ are as defined above,
—N(R$_{2-7}$)—CO—R$_{2-1}$ where R$_{2-1}$ and R$_{2-7}$ are as defined above,
—N(R$_{2-5}$)—CO—O—R$_{2-8}$ where R$_{2-5}$ and R$_{2-8}$ are as defined above,
—N(R$_{2-7}$)—CO—N(R$_{2-5}$)(R$_{2-6}$) where R$_{2-5}$, R$_{2-6}$ and R$_{2-7}$ are as defined above,
—N(R$_{2-7}$)—SO$_2$—R$_{2-4}$ where R$_{2-4}$ and R$_{2-7}$ are as defined above, (3) 2-, 4- and 5-pyrimidinyl optionally substituted with 1 or 2 —$\phi$, or with 1 thru 3 —F, —Cl, —Br, —I, —NO$_2$, —CN, —CF$_3$, C$_1$-C$_{10}$ alkyl, C$_3$-C$_7$ cycloalkyl, —OH, —SH, —NH$_2$,
—O—CO—R$_{2-1}$ where R$_{2-1}$ is as defined above,
—O—S(O)$_2$—R$_{2-4}$ where R$_{2-4}$ is as defined above,
—N(R$_{2-5}$)(R$_{2-6}$) where R$_{2-5}$ and R$_{2-6}$ are as defined above,
—N(R$_{2-7}$)—CO—R$_{2-1}$ where R$_{2-1}$ and R$_{2-7}$ are as defined above,
—N(R$_{2-5}$)—CO—O—R$_{2-8}$ where R$_{2-5}$ and R$_{2-8}$ are as defined above,
—N(R$_{2-7}$)—CO—N(R$_{2-5}$)(R$_{2-5}$) where R$_{2-5}$, R$_{2-6}$ and R$_{2-7}$ are as defined above,
—N(R$_{2-7}$)—SO$_2$—R$_{2-4}$ where R$_{2-4}$ and R$_{2-7}$ are as defined above, (4) 2-, 3- and 4-pyridinyl optionally substituted with 1 or 2 —$\phi$, or with 1 thru 3 —F, —Cl, —Br, —I, —NO$_2$, —CN, —CF$_3$, C$_1$-C$_{10}$ alkyl, C$_3$-C$_7$ cycloalkyl, —OH, —SH, —NH$_2$,
—O—CO—R$_{2-1}$ where R$_{2-1}$ is as defined above,
—O—S(O)$_2$—R$_{2-4}$ where R$_{2-4}$ is as defined above,
—N(R$_{2-5}$)(R$_{2-6}$) where R$_{2-5}$ and R$_{2-6}$ are as defined above,
—N(R$_{2-7}$)—CO—R$_{2-1}$ where R$_{2-1}$ and R$_{2-7}$ are as defined above,
—N(R$_{2-5}$)—CO—O—R$_{2-8}$ where R$_{2-5}$ and R$_{2-8}$ are as defined above,
—N(R$_{2-7}$)—CO—N(R$_{2-5}$)(R$_{2-6}$) where R$_{2-5}$, R$_{2-6}$ and R$_{2-7}$ are as defined above,
—N(R$_{2-7}$)—SO$_2$—R$_{2-4}$ where R$_{2-4}$ and R$_{2-7}$ are as defined above, (5) 2- and 3-thiophenyl optionally substituted with 1 or 2 —$\phi$, or with 1 thru 3 —F, —Cl, —Br, —I, —NO$_2$, —CN, —CF$_3$, C$_1$-C$_{10}$ alkyl, C$_3$-C$_7$ cycloalkyl, —OH, —SH, —NH$_2$,
—O—CO—R$_{2-1}$ where R$_{2-1}$ is as defined above,
—O—S(O)$_2$—R$_{2-4}$ where R$_{2-4}$ is as defined above,
—N(R$_{2-5}$)(R$_{2-6}$) where R$_{2-5}$ and R$_{2-6}$ are as defined above,
—N(R$_{2-7}$)—CO—R$_{2-1}$ where R$_{2-1}$ and R$_{2-7}$ are as defined above,
—N(R$_{2-5}$)—CO—O—R$_{2-8}$ where R$_{2-5}$ and R$_{2-8}$ are as defined above,
—N(R$_{2-7}$)—CO—N(R$_{2-5}$)(R$_{2-6}$) where R$_{2-5}$, R$_{2-6}$ and R$_{2-7}$ are as defined above,
—N(R$_{2-7}$)—SO$_2$—R$_{2-4}$ where R$_{2-4}$ and R$_{2-7}$ are as defined above, (6) 1- and 2-naphthalyl optionally substituted with 1 or 2 —$\phi$, or with 1 thru 7 —F, —Cl, —Br, —I, —NO$_2$, —CN, —CF$_3$, C$_1$-C$_{10}$ alkyl, C$_3$-C$_7$ cycloalkyl, —OH, —SH, —NH$_2$,
—O—CO—R$_{2-1}$ where R$_{2-1}$ is as defined above,
—O—S(O)$_2$—R$_{2-4}$ where R$_{2-4}$ is as defined above,
—N(R$_{2-5}$)(R$_{2-6}$) where R$_{2-5}$ and R$_{2-6}$ are as defined above,
—N(R$_{2-7}$)—CO—R$_{2-1}$ where R$_{2-1}$ and R$_{2-7}$ are as defined above,
—N(R$_{2-5}$)—CO—O—R$_{2-8}$ where R$_{2-5}$ and R$_{2-8}$ are as defined above,
—N(R$_{2-7}$)—CO—N(R$_{2-5}$)(R$_{2-6}$) where R$_{2-5}$, R$_{2-6}$ and R$_{2-7}$ are as defined above,
—N(R$_{2-7}$)—SO$_2$—R$_{2-4}$ where R$_{2-4}$ and R$_{2-7}$ are as defined above:

(7) 2-thiazolyl optionally substituted with 1 or 2 —F, —Cl, —Br, C$_1$-C$_4$ alkoxy, C$_1$-C$_4$ alkyl or —$\phi$,
(8) 2-benzothiazoyl optionally substituted with 1 thru 4 —OH or C$_1$-C$_4$ alkoxy,
(9) C$_1$-C$_4$ alkyl,
(10) C$_3$-C$_6$ cycloalkyl, (R$_3$/R$_4$-I) R$_3$ and R$_4$ together with the attached carbon atom form a cycloalkyl ring of 3 thru 7 carbon atoms,
(R$_3$/R$_4$-II) R$_3$ is —H and R$_4$ is —H, R$_{2-4}$, —CO—O—R$_{2-8}$, —CO—R$_2$, —CN, —CO—NH—R$_2$, —NH—CO—R$_{2-1}$, —S—R$_{2-1}$ and —CO—NH—thiadiazole optionally substituted with —$\phi$ where R$_2$, R$_{2-1}$, R$_{2-4}$ and R$_{2-8}$ are as defined above,
(R$_3$/R$_4$-III) R$_3$ is —H and R$_4$ is —F, —Cl, —Br or —I,
(R$_3$/R$_4$-IV) R$_3$ and R$_4$ are the same or different and are C$_1$-C$_{10}$ alkyl;
(W$_1$-I) W$_1$ is =O, =S, =N—N(R$_{2-7}$)$_2$ where R$_{2-7}$ is as defined above,
(W$_1$-II) W$_1$ is W$_{1-1}$:W$_{1-2}$ where W$_{1-1}$ and W$_{1-2}$ are the same and are C$_1$-C$_4$ alkoxy, —O—$\phi$, C$_1$-C$_4$ alkylthio or —S—$\phi$,
(W$_1$-III) W$_1$ is W$_{1-3}$:W$_{1-4}$ where W$_{1-3}$ and W$_{1-4}$ are taken together with the attached carbon atom to form a 1,3-dioxane, 1,3-dioxolane, 1,3-dithiane, 1,3-dithiolane or 1,3-oxoathiolane ring system.
(W$_1$-IV) W$_1$ is —H:—W$_{1-5}$ where W$_{1-5}$ is
—OH,
—SH,
—NH$_2$,
—S—W$_{1-6}$ where W$_{1-6}$ is C$_1$-C$_4$ alkyl,
—O—CO—R$_{2-1}$ where R$_{2-1}$ is as defined above,
—O—S(O)$_2$—R$_{2-4}$ where R$_{2-4}$ is as defined above,
—N(R$_{2-5}$)(R$_{2-6}$) where R$_{2-5}$ and R$_{2-6}$ are as defined above,
—N(R$_{2-7}$)—CO—R$_{2-1}$ where R$_{2-1}$ and R$_{2-7}$ are as defined above,
—N(R$_{2-5}$)—CO—O—R$_{2-8}$ where R$_{2-5}$ and R$_{2-8}$ are as defined above,
—N(R$_{2-7}$)—CO—N(R$_{2-5}$)(R$_{2-6}$) where R$_{2-5}$, R$_{2-6}$ and R$_{2-7}$ are as defined above,
—N(R$_{2-7}$)—SO$_2$—R$_{2-4}$ where R$_{2-4}$ and R$_{2-7}$ are as defined above;
X is —(CH$_2$)$_{n2}$— or —(CH=CH)$_{n3}$— where n$_2$ is 0 thru 5 and n$_3$ is 0 thru 2, with the proviso that when R$_4$ is —R$_{2-4}$, m$_1$ is 1, and pharmaceutically acceptable salts thereof.

Also disclosed are bicyclic bisphosphonates of formula (V) where
R$_5$ is —H,
C$_1$-C$_{10}$ alkyl,
—$\phi$ optionally substituted with 1 thru 5 —F, —Cl, —Br, —I, —NO$_2$, —CN, —CF$_3$, C$_1$-C$_{10}$ alkyl, C$_3$-C$_7$ cycloalkyl, —OH, C$_1$-C$_4$ alkoxy, —O—φ, C$_1$-C$_4$ alkylthio, —N—CO—R$_{2\text{-}3}$ where R$_{2\text{-}3}$ is as defined above, naphthalene optionally substituted with 1 or 2 —φ, naphthalene optionally substituted with 1-7 —F, —Cl, —Br, —I, —NO$_2$, —CN, —CF$_3$, C$_1$-C$_{10}$ alkyl, C$_3$-C$_7$ cycloalkyl, —OH, C$_1$-C$_4$ alkoxy, —O—φ, C$_1$-C$_4$ alkylthio or —N(CH$_3$)$_2$, Z is —O—,

—NH—,

—(CH$_2$)$_{n5}$— where n$_5$ is 0, 1 or 2,

—S(O)$_{n5}$— where n$_5$ is as defined above,

—N(Z$_1$)— where Z$_1$ is —H, C$_1$-C$_6$ alkyl, C$_3$-C$_7$ cycloalkyl, —φ, 2-pyridinyl, 3-pyridinyl or 4-pyridinyl, —NS(O)$_2$Z$_2$— where Z$_2$ is C$_1$-C$_{10}$ alkyl, —φ optionally substituted with 1 thru 3 —F, —Cl, —Br, —I, —NO$_2$, —CN, —CF$_3$, C$_1$-C$_{10}$ alkyl, C$_3$-C$_7$ cycloalkyl, —OH, C$_1$-C$_4$ alkoxy, —O—φ, C$_1$-C$_4$ alkylthio, —N—CO—Z$_3$ where Z$_3$ is C$_1$-C$_{10}$ alkyl, C$_3$-C$_7$ cycloalkyl, 2-, 3-, 4-pyridinyl, naphthalene optionally substituted with 1 or 2 —φ, naphthalene optionally substituted with 1-7 —F, —Cl, —Br, —I, —NO$_2$, —CN, —CF$_3$, C$_1$-C$_{10}$ alkyl, C$_3$-C$_7$ cycloalkyl, —OH, C$_1$-C$_4$ alkoxy, —O—φ, C$_1$-C$_4$ alkylthio or —N(CH$_3$)$_2$, where M and R$_1$ are as defined above, and pharmaceutically acceptable salts thereof. It is preferred that the acyclic bisphosphonate (III) be the compounds of EXAMPLES 91 and 97.

Further disclosed are cyclic bisphosphonates of formula (VII) where R$_6$, R$_7$ and R$_8$ are the same or different ad are C$_1$-C$_{10}$ alkyl, —φ optionally substituted with 1 thru 3 —F, —Cl, —Br, —I, —NO$_2$, —CN, —CF$_3$, C$_1$-C$_{10}$ alkyl, C$_3$-C$_7$ cycloalkyl, —OH, C$_1$-C$_4$ alkoxy, —O—φ, C$_1$-C$_4$ alkylthio, —N—CO—R$_{2\text{-}3}$ where R$_{2\text{-}3}$ is as defined above, naphthalene optionally substituted with 1 or 2 —φ, naphthalene optionally substituted with 1-7 —F, —Cl, —Br, —I, —NO$_2$, —CN, —CF$_3$, C$_1$-C$_{10}$ alkyl, C$_3$-C$_7$ cycloalkyl, —OH, C$_1$-C$_4$ alkoxy, —O—φ, C$_1$-C$_4$ alkylthio or —N(CH$_3$)$_2$, and where M, R$_1$, R$_5$ and Z are as defined above, and pharmaceutically acceptable salts thereof.

Also disclosed is are keto bisphosphonates of the formula

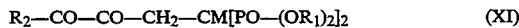

$$R_2\text{—CO—CO—CH}_2\text{—CM[PO—(OR}_1)_2]_2 \qquad (XI)$$

where R$_1$, R$_2$ and M are as defined above, and pharmaceutically acceptable salts thereof.

DETAILED DESCRIPTION OF THE INVENTION

The acyclic bisphosphonates (III) are prepared by contacting an electron deficient olefin (I) with an activated methylene (II) in the presence of a base. This reaction is so well known when the electron withdrawing group is a carbonyl group that it is termed the Michael Reaction, Michael Addition or 1,4-addition. For a review of this reaction see H. O. House, Modern Synthetic Reactions, Second Edition, W. A. Benjamin, Inc., Menlo Park, Calif. (1972), p 595-623. However, when phosphorous is the electron withdrawing group see WO 88/06158.

The electron deficient olefins (I) and activated methylenes (II) are either known to those skilled in the art or can be readily prepared by means known to those skilled in the art from known compounds. Suitable bases include methoxide, ethoxide, DBU, DBN, butyl lithium, methyl lithium, carbonate, bicarbonate, lithium hemamethyldisilazane (in THF or pyridine), hydride, lithium diisopropylamide. It is preferred that the base be DBU, lithium hexamethyldisilane or carbonate depending on the nature of the particular activated methylene (II), bicyclic ketone (IV) or cyclic ketone (VI).

In the case where one of R$_3$ or R$_4$ is not —H, then the reaction is practiced by refluxing the electron deficient olefin (I), activated methylene (II) and base for about 0.5 to about 24 hours. After refluxing the mixture is diluted with water, extracted with an organic solvent such as methylene chloride, dried and concentrated under reduced pressure. The concentrate is preferably purified by (column) chromatography, distillation or crystallization as is know to those skilled in the art. When R$_3$ and R$_4$ are both -H the activated methylene (II), usually a methyl ketone, is first cooled to about 0° to about −78°, contacted slowly with a reagent such as lithium hexamethyldisilazane, and stirred a short period of about 15 minutes to about 1 hr. The electron deficient olefin (I) is then added to the reaction mixture stirred cold (about 0°) for a short period (about 30 min) and then permitted to warm (about 20°-25°) and stirred for another short period (about 30 min).

It is preferred that M is —H. It is preferred that R$_1$ is —H (or a pharmaceutically acceptable salt thereof), C$_1$-C$_2$ alkyl or —CH$_2$—C(CH$_3$)$_2$—CH$_2$— to form a heterocyclic ring containing one phosphorous atom, two oxygen atoms, and three carbon atoms. It is more preferred that R$_1$ is a heterocyclic ring of where the atoms are arranged as follows —P*(O)—O—CH$_2$—C(CH$_3$)$_2$—CH$_2$—O*— where the atoms marked by the asterisk (*) are bonded to each other resulting in the formation of a ring. It is more preferred that R$_1$ is —H or C$_2$ alkyl. It is preferred that R$_2$ is 2-pyridinyl, 3-pyridinyl, 2-furanyl, 2-thienyl or —φ optionally substituted with 1 thru 3 —OH, —F, —Cl, —N(R$_{2\text{-}7}$)—CO—R$_{2\text{-}1}$ where R$_{2\text{-}7}$ is —H and R$_{2\text{-}1}$ is C$_1$ alkyl, C$_2$ alkyl, —φ optionally substituted with —Cl or —NO$_2$. It is more preferred that R$_2$ be 2-pyridinyl, 3-pyridinyl, 2-furanyl, 2-thienyl or —φ optionally substituted with 1 thru 2 —F, —Cl, —N(R$_{2\text{-}7}$)—CO—R$_{2\text{-}1}$ where R$_{2\text{-}7}$ is —H and R$_{2\text{-}1}$ is C1 alkyl, C$_2$ alkyl or —φ. It is even more preferred that R$_2$ be —φ. It is preferred that R$_3$ is —H. It is preferred that R$_4$ is —H, R$_{2\text{-}4}$, —CO—O—R$_{2\text{-}8}$, —CO—R$_2$, —CN and —CO—NH—R$_2$. It is more preferred that R$_4$ be —H, or —φ. It is preferred that m is 1. It is preferred that W$_1$ is ═O. It is preferred that X is not present, that n$_2$ and n$_3$ be 0.

When it is desired that W$_1$ is —H:W$_{1\text{-}5}$ where W$_{1\text{-}5}$ is —OH, those compounds can readily be prepared from compounds where W is ═O by reduction of the ketone carbonyl to the corresponding alcohol by reaction with a mild reducing agent such as sodium borohydride. This type of reduction is well known to those skilled in the art. The use of stronger reducing agents (lithium aluminum hydride) results in reduction of the phosphonate groups. See, EXAMPLES 70 and 71.

When M is —CH$_3$, these compounds can be obtained by deprotonating the starting material under kinetic conditions with a strong base such as lithium hexamethyldisilzane or lithium diisopropyl amide and trapping the resulting anion with an appropriate electrophile. See, EXAMPLE 44.

The phosphonate esters can be convened to the corresponding acids as is well known to those skilled in the art. The phosphonate esters are cleaved using trimethylsilyl bromide in chloroform followed by treatment with water or by refluxing the esters in strong mineral acid. See, EXAMPLES 75-79.

When $R_3$ and $R_4$ are not the same, the bisphosphonates have an asymmetric center at the carbon to which $R_3$ and $R_4$ are attached. The enantiomers can be separated as discussed below.

The bicyclic bisphosphonates (V) are prepared by contacting an electron deficient olefin (I) with a bicyclic ketone (IV) in the presence of a base analogously to the production of the acyclic bisphosphonates (III), see EXAMPLES 4, 25-29, 37, 38 and 77. It is preferred that M is —H. It is preferred that $R_1$ is as set forth above for the bisphosphonates (III). It is preferred that Z is —O—, —S—, —CH$_2$— or —N(SO$_2$—$\phi$)—, it is more preferred that Z is —O— or —CH$_2$—. It is preferred that $R_5$ is —H, C$_1$-C$_4$ alkyl, —$\phi$ optionally substituted with 1 thru 3 —F, —Cl, —Br, —I, —OH, C$_1$-C$_4$ alkoxy, —NH$_2$ and C$_1$-C$_4$ alkyl, it is more preferred that $R_5$ is —H, —CH$_3$ or —$\phi$.

With the bicyclic bisphosphonates (V) when $R_5$ is not —H there exists cis and trans isomers. Both are pharmacologically active and are included by the term bicyclic bisphosphonate and within the formula of the bicyclic bisphosphonate (V). With the bicyclic bisphosphonates (V) there is an asymmetric center where the phosphonate side chain attaches to the bicyclic ring system and therefore produce two enantiomers one "S" and the other "R", either of which can be (+/d) and the other (—/l). If it is desired to utilize one of the enantiomers, the optically impure mixture can be resolved by means known to those skilled in the art, see for example, Optical Resolution Procedures for Chemical Compounds, Vol 1,: Amines and Related Compounds, Paul Newman, Optical Resolution Information Center, Manhattan College, Riverdale, N.Y., 10471, 1978. For example, treatment of the racemic mixture with an optically active amino alcohol such as (—) ephedrine or alternatively with (+) ephedrine, would yield a mixture of diastereomeric isoxalidines, which can be separated most conveniently by fractional crystallization to give a isoxalidine containing only one enantiomer of the racemic mixture. By reacting the diastereomeric isoxalidine with an acid one obtains the desired enantiomer as the free bicyclic bisphosphonate. These optically pure compounds are then used in the same way as the racemic mixture. When used in this patent application the term bicyclic bisphosphonate (V) includes both enantiomers as well as optically impure forms thereof, the most common of which is a racemic mixture (+, dl).

When $R_5$ is not —H, there exists two asymmetric centers and therefore four enantiomers (SS, RR, SR, RS) exist producing two diasteromeric pairs of enantiomers, one SS,RR and the other SR,RS. The diastereomeric pairs of enantiomers can be readily separated by means known to those skilled in the art. When used in this patent application the term bicyclic bisphosphonate (V) includes all four enantiomers as well as optically impure forms thereof, the most common of which is a racemic mixture (+). The cyclic bisphosphonates (VII) are prepared by contacting an electron deficient olefin (I) with a cyclic ketone (VI) in the presence of a base analogously to the production of the acyclic bisphosphonates (III), see EXAMPLES 30 and 31. It is preferred that $R_1$ is as set forth above for the bisphosphonates (III). It is preferred that Z is —O—, —S—, —CH$_2$— and —N(SO$_2$—$\phi$)—, it is more preferred that Z is —CH$_2$—. It is preferred that $R_5$ is —H, C$_1$-C$_4$ alkyl, —$\phi$ optionally substituted with 1 thru 3 —F, —Cl, —Br, —I, —OH, C$_1$-C$_4$ alkoxy, —NH$_2$ and C$_1$-C$_4$ alkyl, it is more preferred that $R_5$ is —H. It is preferred that $R_6$ and $R_8$ are —H. It is preferred that $R_7$ is C$_1$ or C$_2$ alkyl or —$\phi$, it is more preferred that $R_7$ is C$_1$ alkyl or —$\phi$. It is more preferred that at least two of $R_6$, $R_7$ and $R_8$ are —H, it is even more preferred that at all three of $R_6$, $R_7$ and $R_8$ are —H.

CHART D discloses that the keto bisphosphonates (XI) are synthesized by treating electron deficient olefins (I) with a metal acetylide (IX) in a nonpolar solvent at a temperature below 0°. The metal can be lithium, sodium, or potassium and acceptable solvents include THF, DME, ether, and hexane. It is preferred that the metal is lithium, the solvent THF, and the temperature —78°. Generation of the metal acetylide is well known to those skilled in the art. The initial adduct is purified by chromatography, distillation, or recrystallization.

The diphosphonate acetylide (X) is converted to the keto bisphosphonate under oxidizing conditions which are well known to those skilled in the art. The oxidant can be potassium permanganate, ruthenium tetroxide, or ruthenium dioxide in the presence of sodium periodate, and the reaction can be run in a polar solvent such as acetone or methyl ethyl ketone at temperatures between 22° and reflux. It is preferred that the oxidant be potassium permanganate and that the reaction be run in a mixture of a non-polar solvent such as methylene chloride, chloroform, benzene, or toluene and an immiscible, polar solvent such as water in the presence of a phase transfer catalyst, as is well known to those skilled in the art.

The preferred pharmaceutically acceptable cation salts include sodium, potassium, ammonium, calcium, magnesium, tromethamine (THAM), 2-amino-2-(hydroxymethyl)-1,3-propanediol, t-butyl—NH$_3$+ and HO—CH$_{2CH}$2—NH$_3$+.

The acyclic bisphosphonates (III), bicyclic phosphonates (V), cyclic bisphosphonates (VII) and keto bisphosphonates (XI) have the same or similar pharmacological activity of being useful as anti-arthritic agents. For convenience, the acyclic bisphosphonates (III), bicyclic phosphonates (V), cyclic bisphosphonates (VII) and keto bisphosphonates (XI) will be identified by the term bisphosphonates. The bisphosphonates (III, V, VII and XI) are useful in humans and lower animals in the treatment of diseases characterized by abnormal phosphate and calcium metabolism and as a treatment of inflammation. These diseases include osteoporosis, Paget's disease, periodontal disease, rheumatoid arthritis, osteoarthritis, chondrocalcinosis, septic arthritis, neurilities, bursitis, soft tissue mineralization disorders, ankylosing spondylitis, atherosclerosis, multiple myeloma of bone, metastatic bone disease, chronic granulomatous diseases and mitral valve calcification.

The bisphosphonates are also useful for the treatment of hypertension, congestive heart failure and atherogenesis.

The bisphosphonates (III, V and VII) can be administered orally, parenterally (intramuscularly, intravenously, subcutaneous or intraperitoneally), transdermally or intraarticularly or by suppository. The dose is about 0.1 nag/patient/day to about 1.0 gin/patient/day.

The bisphosphonates (III, V and VII) can be used alone or in combination with other pharmaceutical as is known to those skilled in the art.

The exact dosage and frequency of administration depends on the particular bisphosphonate (III, V or VII), the particular condition being treated, the severity of the condition being treated, the age, weight, general physical condition of the particular patient, the severity of the disease or condition, other medication the individual may be taking as is well known to those skilled in the art and can be more accurately determined by measuring the blood level or concentration of the bisphosphonate (III, V or VII) in the patient's blood and/or the patient's response to the particular condition being treated.

For the diseases outlined above, intermittent therapy is indicated, as well as continual daily therapy in order to achieve maximum efficacy as is known to those skilled in the art. See, for example, "Long-Term Effects of Dichloromethylene Diphosphonate in Paget's Disease of Bone", P. D. Dumas et al, J. Cln. Endocrinol. Metab., 54, 837 (1982); "Paget's Disease of Bone Treated in Five Days With AHPrBP(APD) Per Os", D. Thiebaud et at, J. Bone. Min. Res., 2, 45 (1987); "A Single Infusion of the Bisphosphonate AHPrBP(APD)", D. Rischin et al, Aust. NZ. J. Med., 18, 736 (1988); "Reduced Morbidity From Skeletal Metastases in Breast Cancer Patients during Long Term Biophoshonate (APD) Treatment" A. Th. van Holten-Verzantviiort et al, The Lancet, Oct. 31, 1987, p.983; "Sclerosis of Lytic Bone Metastases After Disodium Aminohydroxypropylidene Bisphosphonate (APD) in Patients with Breast Carcinoma" A. R. Morton et all, British Med. J., 297, 772 (1988); "Two Year Follow-up of Biophosphionate (APD) Treatment in Steroid Osteoporosis" I. R. Reid et at, The Lancet Nov. 12, 1988, p. 1144.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3—C(=Z_1)H$. Groups $R_i$ and $R_j$ would represent monovalent variable substituents if attached to the formula $CH_3—CH_2—C(R_i)(R_j)H_2$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the an of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3—O—CH_2—CH(R_i)—CH_3$ represents a 2-substituted-1-methoxypropane compound. In a similar fashion, the symbol "=" represents a double bond, e.g., $CH_2=C(R_i)—O—CH_3$, and the symbol "≡" represents a triple bond, e.g., $HC≡C—CH(R_i)—CH_2—CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by $N^*=C(CH_3)—CH=CCl—CH=C^*H$ with the convention that the atoms marked with an asterisk (*) are bonded to each other resulting in the formation of a ring. Likewise, the cyclic molecular fragment, 4-(ethyl)-1-piperazinyl can be represented by $—N^*—(CH_2)_2—N(C_2H_5)—CH_2—C^*H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, $—C(X_1)(X_2)—$ the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha ($\alpha$) configuration and is identified by a broken, dashed or dotted line attachment to the carbon atom, i.e., by the symbol "- - -" or ". . .". The corresponding substituent attached "above" ($X_2$) the other ($X_1$) is identified as being in the beta ($\beta$) configuration and is indicated by an unbroken line attachment to the carbon atom.

When a variable substituent is bivalent, the valences may be taken together or separately or both in the definition of the variable. For example, a variable $R_i$ attached to a carbon atom as $—C(=R_i)—$ might be bivalent and be defined as oxo or keto (thus forming a carbonyl group (—CO—) or as two separately attached monovalent variable substituents $\alpha$-$R_{i-j}$ and $\beta$-$R_{i-k}$. When a bivalent variable, $R_i$, is defined to consist of two monovalent variable substituents, the convention used to define the bivalent variable is of the form "$\alpha$-$R_{i-j}$:$\beta$-$R_{i-k}$" or some variant thereof. In such a case both $\alpha$-$R_{i-j}$ and $\beta$-$R_{i-k}$ are attached to the carbon atom to give —C($\alpha$-$R_{i-j}$)($\beta$-$R_{i-k}$)—. For example, when the bivalent variable $R_6$, $—C(=R_6)—$ is defined to consist of two monovalent variable substituents, the two monovalent variable substituents are $\alpha\text{-R}_{6\text{-}1}:\beta\text{-R}_{6\text{-}2}, \ldots \alpha\text{-R}_{6\text{-}9}:\beta\text{-R}_{6\text{-}10}$, etc, giving $-C(\alpha\text{-R}_{6\text{-}1})(\beta\text{-R}_{6\text{-}2})-, \ldots -C(\alpha\text{-R}_{6\text{-}9})(\beta\text{-R}_{6\text{-}10})-$, etc. Likewise, for the bivalent variable $R_{11}$, $-C(=R_{11})-$, two monovalent variable substituents are $\alpha\text{-R}_{11\text{-}1}:\beta\text{-R}_{11\text{-}2}$. For a ring substituent for which separate $\alpha$ and $\beta$ orientations do not exist (e.g. due to the presence of a carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula $-C_1(R_i)H-C_2(R_j)H-$ ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation "... $R_i$ and $R_j$ are taken together to form $-CH_2-CH_2-O-CO-$..." means a lactone in which the carbonyl is bonded to $C_2$. However, when designated "... $R_j$ and $R_i$ are taken together to form $-CO-O-CH_2-CH_2-$" the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxycarbonyl describes a group $CH_3-(CH_2)_n-O-CO-$ where n is zero, one or two. By the second method the carbon atom content of only each portion of the definition is indicated separately by enclosing the "$C_i$-$C_j$" designation in parentheses and placing it immediately (no intervening space) before the portion of the definition being defined. By this optional convention ($C_1$-$C_3$)alkoxycarbonyl has the same meaning as $C_2$-$C_4$ alkoxycarbonyl because the "$C_1$-$C_3$" refers only to the carbon atom content of the alkoxy group. Similarly while both $C_2$-$C_6$ alkoxyalkyl and ($C_1$-$C_3$)alkoxy($C_1$-$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. DEFINITIONS

All temperatures are in degrees Centigrade.
TLC refers to thin-layer chromatography.
THF refers to tetrahydrofuran.
DMF refers to dimethylformamide.
LiHMDS refers to lithium hemamethyldisilazane.
DBU refers to 1,8-diazabicyclo[5.4.0]undec-7-ene.
Saline refers to an aqueous saturated sodium chloride solution.
IR refers to infrared spectroscopy.
CMR refers to C-13 magnetic resonance spectroscopy, chemical shifts are reported in ppm ($\delta$) downfield from TMS.
NMR refers to nuclear (proton) magnetic resonance spectroscopy, chemical shifts are reported in ppm $\delta$) downfield from tetramethylsilane.
TMS refers to trimethylsilyl.
—$\phi$ refers to phenyl ($C_6H_5$).
MS refers to mass spectrometry expressed as m/e or mass/charge unit. [M +H]+ refers to the positive ion of a parent plus a hydrogen atom. EI refers to electron impact. CI refers to chemical ionization. FAB refers to fast atom bombardment.
Ether refers to diethyl ether.
Alcohol refers to ethyl alcohol.
Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.
When solvent pairs are used, the ratios of solvents used are volume/volume (v/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1

2,2'-Methylenebis[5,5-dimethyl-2,2'-dioxide-1,3,2-dioxaphosphorinane]

Methylene bisphosphonic acid (12.8 g) is combined with methylene bis(diethylphosphonate) (20.9 g) and the mixture is heated until the solid is completely dissolved (ca. 185°). Phosphorus pentachloride (121 g) is added to the solution (20°-25°) in small portions over 1 hour. The mixture is stirred 30 minutes then diluted with hexane (300 ml) and stirred an additional 30 minutes. The mixture is filtered, the methylene bisphosphonylchloride solid is washed with cold hexane and dried briefly.

The crude tetra-acid chloride (methylene bisphosphonylchloride) is combined with 2, 2-dimethyl-1,3-propanediol (17.5 g) in chlorobenzene (80 ml) and refluxed for 20 hours. The mixture is cooled, the solvent is removed under reduced pressure to give a solid. The solid is recrystallized from acetone to give the title compound, mp 193°–194°; MS (m/e) 312, 297, 257, 227 and 69; IR (mineral oil) 1491, 1476, 1407, 1354, 1312, 1282, 1272, 1180 and 1052 cm$^{-1}$; NMR (CDCl$_3$) 4.24–4.18, 4.11–4.03, 2.73, 1.20 and 1.00 δ.

PREPARATION 2

2,2'-Ethenylidenebis[5,5-dimethyl-2,2'-dioxide-1,3,2-dioxaphosphorinane] (I)

2,2'-Methylenebis[5,5-dimethyl-2,2'-dioxide 1,3,2-dioxaphosphorinane] (PREPARATION 1, 10.05 g) is dissolved in a warm solution of methanol (90 ml) containing paraformaldehyde (5.02 g) and diethylamine (3.3 ml) and gently refluxed for 2.5 hours. The mixture is cooled and the solvents removed by reduced pressure and mild heat. The residue is dissolved in toluene (40 ml) and a strongly acidic ion exchange resin is added and the mixture refluxed through a Dean-Stark trap for 80 min. The mixture is cooled and the solvents removed by reduced pressure with mild heat. The residue is recrystallized from acetone to give the title compound, mp 193°–194°; MS (m/e) 324, 309, 269, 239 and 171; IR (mineral oil) 1574, 1464, 1384, 1371. 1281, 1247 and 1054 cm$^{-1}$; NMR (CDCl$_3$) 6.95, 6.82, 4.18, 4.02, 1.30 and 0.93 δ; CMR (CDCl$_3$) 146.6, 138.8, 32.5, 22.0 and 20.7 δ.

EXAMPLE 1

[4-Oxo4-(2-thiazolylamino)-2-[(2-thiazolylamino)carbonyl]butylidene]bisphosphonic acid, tetraethyl ester (III)

Part A

Diethyl malonate (7.6 ml) and 2-aminothiazole (5.0 g) are added to a solution of sodium ethoxide, prepared from sodium (2.3 g) in ethanol (50 ml). The reaction mixture is refluxed for 2.5 hours, then cooled in ice, treated with concentrated hydrochloric acid (11 ml). The precipitate which forms is filtered. The bis 2-aminothiazole malonate amide (II) is recrystallized from ethanol and is used in Part B without further characterization, NMR (D$_2$O/sodium hydroxide) 7.3 and 6.8 δ.

Part B

Ethenylidenebisphosphonic acid tetraethyl ester (I, EP 221.611, 4.50 g) the N,N'-bis (2-thiazolyl)malonamide (II, 2.52 g), and DBU (0.25 ml) are heated in refluxing ethanol (50 ml) for 18 hours. The reaction mixture is concentrated under reduced pressure and subjected directly to chromatography (ethyl acetate/acetone, 1/1). The appropriate fractions are pooled and concentrated to give the tide compound which is then recrystallized from methanol/water, mp 188°–188.5°; MS (m/e) 568 (M+), 469, 423, 331 and 281; IR (mineral oil) 1701, 1678, 1566 and 1264 cm$^{-1}$; NMR (CDCl$_3$) 7.30, 6.83, 4.57, 4.38, 4.23, 3.39, 2.86, 1.42 and 1.26 δ.

EXAMPLE 2

(3-Acetyl-4-ethoxy-4-oxobutylidene)bisphosphonic acid tetraethyl ester (III)

Ethenylidenebisphosphonic acid tetraethyl ester (I, 3.00 g), ethyl acetoacetate (II, 1.4 ml), and DBU (0.25 ml) are heated to 500 in THF (20 ml) for 1.5 hours. The reaction is cooled, diluted with ethyl acetate, filtered through magnesium sulfate and concentrated under reduced pressure. The concentrate is chromatographed eluting with ethyl acetate, ethyl acetate/acetone (1/1). The appropriate fractions are pooled and concentrated to give the title compound, MS (m/e) 430 (M+), 388, 339, 301 and 288; IR (neat) 2984, 1740, 1716, 1478, 1444, 1392, 1368 and 1250 cm$^-$; NMR (CDCl$_3$) 4.20, 2.43, 2.29, 1.35 and 1.28 δ.

EXAMPLE 3

(3,3-Dibenzoylpropylidene)bisphosphonic acid tetraethyl ester (III)

Ethenylidenebisphosphonic acid tetraethyl ester (I, 3.00 g), dibenzoyl methane (II, 2.30 g), and DBU (0.25 ml) are heated to 50° in THF (20 ml) for 15 min. The reaction mixture is cooled, diluted with ethyl acetate, filtered through magnesium sulfate and concentrated under reduced pressure. The concentrate is chromatographed eluting with ethyl acetate, ethyl acetate/acetone (1/1). The appropriate fractions are pooled and concentrated to give the title compound, MS (m/e) 524 (M+), 419, 387, 373, 268 and 224; IR (neat) 2982, 1736, 1696, 1674, 1594, 1580, 1448, 1392 and 1253 cm$^{-1}$; NMR (CDCl$_3$) 8.07, 7.58, 7.46, 6.18, 4.17, 2.65 and 1.29 δ.

EXAMPLE 4

[2-(4-Oxo-1-(tosyl)-1,2,3,4-tetrahydroquinolin-3-yl)ethylidene]bisphosphonic acid tetraethyl ester (V)

Aniline (36.4 ml), methyl acrylate (38.5 ml) and acetic acid (1 ml) are refluxed for 18 hours, then distilled, bp$_{0.4}$ 120°–125°.

To a solution of the above mixture (50.0 g) in pyridine (250 ml), tosyl chloride (58.0 g) is added over a period of 10 min. After 15 min at 22°, the reaction is heated on the stem bath for 15 min, then just to boiling on a hot plate. The cooled reaction is then diluted with ether, washed with hydrochloric acid (10%, 4 times), sodium bicarbonate (twice) and saline, then dried with magnesium sulfate, and concentrated under reduced pressure to give the crude ester.

The crude ester in methanol (80%, 500 ml) is treated slowly with potassium hydroxide (10%, 200 ml) and stirred overnight. The reaction is poured onto water (500 ml) and acidified with concentrated hydrochloric acid. The precipitate is collect, then dissolved in sodium bicarbonate solution, filtered, acidified with hydrochloric acid (10%), and filtered. The product is recrystallized from toluene, mp 139°–141°.

A mixture of the acid (15.97 g) and phosphorous pentachloride (10.4 g) in toluene (100 ml) is heated to reflux for 30 min, then the reaction is cooled to 0°, and treated with tin tetrachloride (8.8 ml) in toluene (40 ml). After 15 min at 0° and 18 hours at 22°, the mixture is poured on to concentrated hydrochloric acid/ice, extracted with ethyl acetate (3×), washed with water, saturated sodium bicarbonate, and saline, dried with magnesium sulfate, and concentrated under reduced pressure. The N-tosyl-4-oxo-1,2,3,4-tetrahydroisoquinoline (II) is recrystallized (2×) from 95% ethanol.

The ketone (II, 4.27 g), ethenylidenebisphosphonic acid tetraethyl ester (I, 3.60 g) and DBU (2 ml) are stirred in THF (30 ml) for 1 hour. The reaction is diluted with ethyl acetate, washed with hydrochloric acid (IN), saturated sodium bicarbonate, and saline, dried with magnesium sulfate, and concentrated under reduced pressure. The product is chromatographed eluting with ethyl acetate/ethyl acetate-acetone 1/1) to give the title compound, MS (m/e) 601, 446, 400, 372 and 155; IR (neat) 2983, 1689, 1599, 1574, 1494, 1477, 1392 and 1254 cm$^{-1}$; NMR (CDCl$_3$) 7.95, 7.8, 7.7, 7.49, 7.28, 7.14, 4.47, 4.20, 3.79, 3.14, 2.83, 2.4, 1.93 and 1.32 δ.

EXAMPLE 5

[3-(2-Pyridinylamino-carbonyl)-4-oxo-4-phenyl-butylidene]bisphosphonic acid tetraethyl ester (III)

Ethyl benzoyl acetate (9.5 ml) and 2-aminopyridine (4.71 g) are heated to 1400 under house vacuum for 2 hours. The reaction is cooled, and the resulting oil triturated with ether to give a precipitate. The precipitate is filtered, washed with ether, and recrystallized from acetonitrile to give an amide, N-(2-pyridinyl)-3-oxo-3-phenylpropanamide (II).

The amide (II, 2.52 g), ethenylidenebisphosphonic acid tetraethyl ester (I, 3.00 g), and DBU (0.25 ml) are heated to 50° C. in THF (20 ml) for 3 hrs. The reaction is cooled, diluted with ethyl acetate, then extracted with hydrochloric acid (10%, 3×). After back washing with ethyl acetate, the acidic fraction is neutralized with saturated sodium bicarbonate, extracted with methylene chloride, dried with magnesium sulfate, and concentrated under reduced pressure. The crude material is chromatographed eluting with ethyl acetate and acetone. The resulting oil is concentrated under reduced pressure from ether to give a solid. The solid is slurried in ether, filtered and dried under reduced pressure to give the title compound, mp 104°-105°; MS (m/e) 540, 435, 420, 403, 163, 121, 105 and 94; IR (mineral oil) 1705, 1679, 1596, 1578, 1543, 1435 and 1256 cm$^{-1}$; NMR (CDCl$_3$) 9.77, 8.28, 8.10, 7.60, 7.47, 7.01, 5.16, 4.16, 2.65, 1.34 and 1.26 δ; CMR (CDCl$_3$) 202.9, 195.5, 167.6, 151.1, 147.6, 138.4, 136.0, 133.7, 128.9, 128.7, 119.9, 114.1, 63.0 (m), 54.1, 34.5, 25.9 and 16.3 δ.

EXAMPLE 6

(4-Anilino-3-benzoyl-4-oxobutylidene)bisphosphonic acid tetraethyl ester (III)

Ethyl benzoyl acetate (9.5 ml) and aniline (4.6 ml) are heated to 18020 in xylene (20 ml) and the reaction distilled. When the volume is reduced by half, xylene (20 ml) is added and distillation continued. The reaction is cooled and the precipitate filtered. The precipitate is recrystallized once with ethanol/water (1/1), and then again from toluene to give an amide, N-phenyl-3-oxo-3-phenylpropanamide (II).

The amide (II, 2.50 g), ethenylidenebisphosphonic acid tetraethyl ester (I, 3.00 g), and DBU (0.25 ml) are heated to 50° C. in THF (20 ml) for 30 min. The reaction is cooled, diluted with ethyl acetate, washed with hydrochloric acid (1N), saturated sodium bicarbonate, and saline, then dried with magnesium sulfate, and concentrated under reduced pressure. The crude material is chromatographed eluting with ethyl acetate. The compound is left overnight on the bench whereupon a solid formed. This is slurried in ether, filtered and dried in under reduced pressure to give the title compound, mp 104°-105°; MS (m/e) 539, 447, 288, 239, 163, 120, 105 and 93; IR (mineral oil) 1699, 1682, 1606, 1599, 1589, 1549, 1442 and 1241 cm$^{-1}$; NMR (CDCl$_3$) 9.55, 8.08, 7.57, 7.46, 7.30, 7.09, 4.96, 4.17, 2.58, 1.38 and 1.28 δ; CMR (CDCl$_3$) 212.4, 195.5, 167.1, 138.0, 136.2, 133.7, 128.9, 128.8, 128.5, 124.3, 119.6, 63.1 (m), 54.0, 34.5, 25.9 and 16.3 δ.

EXAMPLE 7

[3-(3-Pyridinylamino-carbonyl)-4-oxo-4-phenyl-butylidene]bisphosphonic acid tetraethyl ester hemi hydrate (III)

Ethyl benzoyl acetate (9.5 ml) and 3-aminopyridine (4.71 g) are heated to 1400 under house vacuum for 2 hours. The reaction is cooled, and the oil triturated with ether forming a precipitate. The precipitate is filtered, washed with ether, and recrystallized from ethanol/water to give an amide, N-(3-pyridinyl)-3-oxo-3-phenyl-propanamide (II). The amide (II, 2.52 g), ethenyliden-bisphosphoric acid tetraethyl ester (3.00 g), and DBU (0.25 ml) are heated to 50° C. in THF (20 ml) for 3 hrs. The reaction is cooled, diluted with ethyl acetate, then extracted with hydrochloric acid (10%, 3×). After back washing with ethyl acetate, the acidic fraction is neutralized with saturated sodium bicarbonate, extracted with methylene chloride, dried with magnesium sulfate, and concentrated under reduced pressure. The crude material is chromatographed eluting with ethyl acetate and acetone. The appropriate fractions are pooled and concentrated to give an oil. The oil is concentrated under reduced pressure from ether to give a solid. The solid is slurried in ether, filtered and dried under reduced pressure to give the title compound, mp 108°-109°; MS (m/e) 540, 435, 288, 273, 240 and 163; IR (mineral oil) 1699, 1675, 1605, 1595, 1579, 1548 and 1245 cm$^{-1}$; NMR (CDCl$_3$) 8.66, 8.33, 8.16, 8.07, 7.58, 7.46, 7.23, 5.02, 4.18, 2.62 and 1.34 δ; CMR (CDCl$_3$) 195.1,168.0, 145.0, 140.9, 136.0, 135.1, 133.8, 128.9, 128.5, 126.9, 123.7, 63.2, 53.8, 34.6, 25.7 and 16.3 δ.

EXAMPLE 8

[3-Benzoyl-4-[(6-methoxybenzothiazol-2-yl)amino]-4-oxobutylidene]bisphosphonic acid tetraethyl ester hemihydrate (III)

Ethyl benzoyl acetate (9.5 ml) and 2-amino-6-methoxy benzothiazole (9.01 g) are heated to 140° under house vacuum for 2 hours. After cooling, the residue is taken up in acetone and filtered. The precipitate is dissolved in hot DMF to give an amide, N-(6-methoxyben-zothiazol -2-yl)-3-oxo-3-phenylpropanamide (II).

The amide (II, 2.90 g, ethenylidenbisphosphoric acid tetraethyl ester (2.55 g), and DBU (0.25 ml) are heated to 50° in DMF (10 ml) for 5 days. The reaction is cooled, diluted with ethyl acetate, washed with hydrochloric acid (1N), saturated sodium bicarbonate, and saline, then dried with magnesium sulfate, and concentrated under reduced pressure. The crude material is chromatographed eluting with ethyl acetate, ethyl acetate/acetone (1/1), acetone. The appropriate fractions are pooled and concentrated to give a solid which is recrystallized from alcohol to give the title compound, mp 206°-207°; MS (m/e) 626, 448, 326 and 180; IR (mineral oil) 1705, 1675, 1606, 1572, 1560, 1285 and 1252 cm$^{-1}$; NMR (CDCl$_3$) 8.12, 7.68, 7.59, 7.47, 7.16, 7.01, 5.31, 4.15, 3.84, 2.77 and 1.29 δ.

EXAMPLE 9

[3-Benzoyl-4-[(3-phenyl-1,2,4-thiadiazol-5-yl)amino]-4-oxobutylidene]bisphosphonic acid tetraethyl ester (III)

Ethyl benzoyl acetate (5.2 ml) and 2-amino4-phenyl-1,3,5-thiadiazole (4.99 g) are heated to 1400 under house vacuum for 2 hours. After cooling, the residue is taken up in ether and filtered. The precipitate is then recrystallized from acetonitrile to give an amide, N-(4-phenyl-1,3,5-thiadiazol-2-yl)-3-oxo-3-phenylpropanamide (II).

The amide (II, 3.42 g), ethenylidenbisphosphoric acid tetraethyl ester (3.00 g), and DBU (0.25 ml) are heated to 50° C. in THF (20 ml) for 30 min. After cooling, the reaction is diluted with ethyl acetate, washed with hydrochloric acid (1N), saturated sodium bicarbonate, and saline, then dried with magnesium sulfate, and concentrated under reduced pressure. The crude material is chromatographed eluting with ethyl acetate, ethyl acetate/acetone (1/1). The appropriate fractions are pooled and concentrated to give a solid which is dissolved in ethanol, treated with charcoal, filtered through celite, and concentrated under reduced pressure. The solid is triturated with ether and filtered to give the title compound, mp 162°–167° (dec); MS (m/e) 323, 295, 273, 253, 204 and 177; IR (mineral oil) 1707, 1700, 1682, 1598, 1584, 1565 and 1260 cm$^{-1}$; NMR (CDCl$_3$) 12.5, 8.18, 7.76, 7.4, 5.63, 4.10, 2.75 and 1.24 δ; CMR (CDCl$_3$) 216.5, 195.1, 174.8, 168.5, 167.6, 135.4, 133.8, 133.1, 129.8, 128.9, 128.8, 128.4, 128.0, 63.6, 52.7, 34.3, 25.3 and 16.3 δ.

EXAMPLE 10

[4-(4-Hydroxphenyl)-4-oxo-3-phenylbutylidene)]bisphosphonic acid tetraethyl ester (III)

Phenol (12.2 g) and phenylacetyl chloride (20 g) are heated at 80° for 1 hour in nitrobenzene (115 ml), treated with aluminum trichloride (22.7 g), and heating maintained for 1 hour. The reaction is cooled, then poured onto acidified ice water, extracted twice with ether, and washed with water. The organic phase is extracted with sodium hydroxide (10%), acidified with hydrochloric acid (10%), and cooled in ice. The precipitate is collected and recrystallized from water to give a ketone, 4'-hydroxy-2-phenylacetophenone (II).

The 4'-hydroxy-2-phenylacetophenone (II, 5.860 g), ethenylidenbisphosphoric acid tetraethyl ester (8.28 g) and DBU (4.2 ml, 27.6 mmol) are heated to 500 in THF (30 ml) for 18 hours. The reaction is cooled, diluted with water, extracted with methylene chloride, dried with magnesium sulfate, and concentrated under reduced pressure. The concentrate is then chromatographed (twice) eluting with ethyl acetate, ethyl acetate/acetone (1/1). The appropriate fractions are pooled and concentrated to give the title compound, MS (m/e) 512, 392, 288, 149, 121 and 93; IR (neat) 2983, 1736, 1723, 1704, 1668, 1603, 1583, 1515, 1493, 1477, 1454, 1443 and 1239 cm$^{-1}$; NMR (CDCl$_3$) 7.85, 7.29, 6.80, 5.21, 4.14, 2.60, 2.41, 1.35 and 1.22 δ.

EXAMPLE 11

(4-Oxo-3,4-diphenylbutylidene)bisphosphonic acid tetraethyl ester (III)

Ethenylidenebisphosphonic acid tetraethyl ester (I, 10.0 g) and deoxybenzoin (II, 6.54 g) in a solution of sodium ethoxide, prepared from 50% sodium hydride (1.6 g, 33.3 mmol) and ethanol (50 ml), are refluxed for 21 hours. The mixture is diluted with water, extracted with methylene chloride (3×), dried with magnesium sulfate, and concentrated under reduced pressure. The product is chromatographed eluting with ethyl acetate/methanol (95/5). The appropriate fractions are pooled and concentrated to give the title compound.

EXAMPLE 11A (4-Oxo-3,4-diphenylbutylidene)bisphosphonic acid tetraethyl ester (III)

Alternative and Preferred Method

Ethenylidenebisphosphonic acid tetraethyl ester (I, 2.70 g), deoxybenzoin (II, 1.96 g), and DBU (0.15 ml) are healed to 50° in THF (10 ml) for 40 hours. The reaction is cooled diluted with methylene chloride, washed with water, dried with magnesium sulfate, and concentrated under reduced pressure. The residue is chromatographed eluting with ethyl acetate, ethyl acetate/acetone (1/I). The appropriate fractions are pooled and concentrated to give the title compound, MS (m/e) 496, 288, 243 and 105; IR (neat) 2983, 1681, 1253, 1065, 1042, 1028 and 972 cm$^{-1}$; NMR (CDCl$_3$) 7.98, 7.45, 7.32, 7.23, 5.28, 4.1, 3.9, 2.6, 2.4, 1.35, 1.25 and 1.18 δ; CMR (CDCl$_3$) 199, 138, 136, 133, 128.9, 128.6, 128.4, 128.3, 127, 62, 51, 34, 30 and 16 δ.

EXAMPLES 12–38

Following the general procedure of EXAMPLES 1–11 using DBU as the base and making non-critical variations but starting with the appropriate electron deficient olefin (I) and activated methylene (II), bicyclic ketone (IV) or cyclic ketone (VI), the title compounds are obtained.

EXAMPLE 12

(3-Benzoyl-4-ethoxy4-oxobutylidene)bisphosphonic acid tetraethyl ester (III)

Ethenylidenebisphosphonic acid tetraethyl ester (I) and ethyl benzoyl acetate (II), MS (m/e) 492, 387, 355, 301 and 288; IR (neat) 2983, 1738, 1685, 1597, 1581, 1448, 1392, 1369 and 1251 cm$^{-1}$; NMR (CDCl$_3$) 8.08, 7.61, 7.49, 5.10, 4.17, 2.58, 1.35 and 1.17 δ.

EXAMPLE 13

(3-Methyl4-oxo-4-phenylbutylidene)bisphosphonic acid tetraethyl ester (III)

Ethenylidenebisphosphonic acid tetraethyl ester (I) and propiophenone (II), MS (m/e) 434, 392, 329, 297, 288, 261,243, 152, 132 and 105; IR (neat) 2983, 1682, 1253, 1027 and 970 cm$^{-1}$; NMR (CDCl$_3$) 8.03, 7.57, 7.47, 4.1, 2.4, 2.0 and 1.29 δ; CMR (CDCl$_3$) 203, 136, 133, 128.6, 128.5, 62, 38, 34, 29, 17 and 16 δ.

EXAMPLE 14

[4-(4-Bromophenyl)-4-oxo-3-phenylbutylidene]bisphosphonic acid tetraethyl ester (III)

Ethenylidenebisphosphonic acid tetraethyl ester (I) and 4'-bromo-2-phenylacetophenone (II), MS (m/e) 577, 575, 547, 497, 391,301 and 183; IR (neat) 2981, 1681, 1584, 1554, 1395 and 1252 cm$^{-1}$; NMR (CDCl$_3$) 7.83, 7.50, 7.25, 5.23, 4.1, 2.63, 2.40, 1.37, 1.26 and 1.19 δ.

EXAMPLE 15

[4-Oxo4-(4-biphenyl)-3-phenylbutylidene]bisphosphonic acid tetraethyl ester hemihdrate (V)

Ethenylidenebisphosphonic acid tetraethyl ester (I) and 2,4'-diphenylacetophenone (II), MS (m/e) 573, 545, 391,301 and 181; IR (neat) 2982, 1677, 1603, 1582, 1454, 1405, 1392 and 1252 cm$^{-1}$; NMR (CDCl$_3$) 8.07, 7.58, 7.38, 5.32, 4.3–3.87, 2.70, 2.42 and 1.32 δ.

EXAMPLE 16

[4-(4-Methoxyphenyl)4-oxo-3-(phenylbutylidene]bisphosphonic acid tetraethyl ester hemihydrate (III)

Ethenylidenebisphosphonic acid tetraethyl ester (I) and 4'-methoxy-2-phenylacetophenone (II), MS (m/e) 527, 499, 481,301 and 135; IR (neat) 2982, 1671, 1599, 1575, 1512, 1493, 1476, 1454 and 1251 cm$^{-1}$; NMR (CDCl$_3$) 7.98, 7.25, 6.85, 5.23, 4.34.0, 3.90, 3.80, 2.63, 2.45, 1.37, 1.26 and 1.18 δ.

EXAMPLE 17

α-[2,2-Bis(ethoxyphosphinyl)ethyl]-benzene acetic acid methyl ester (III)

Ethenylidenebisphosphonic acid tetraethyl ester (I) and methyl phenyl acetate (II), MS (m/e) 450, 418, 390 and 288; IR (neat) 2983, 1735, 1601, 1584, 1494, 1478 and 1255 cm$^{-1}$; NMR (CDCl$_3$) 7.31, 4.01, 3.57, 2.40 and. 1.27 δ.

EXAMPLE 18

(3-Cyano-3-phenylpropylidene)bisphosphonic acid tetraethyl ester (III)

Ethenylidenebisphosphonic acid tetraethyl ester (I) and phenyl acetonitrile (II), MS (m/e) 417, 288, 261 and 233; IR (neat) 2984, 2242, 1601, 1587, 1494, 1478, 1456, 1,444 and 1256 cm$^{-1}$; NMR (CDCl$_3$) 7.38, 4.45, 4.15, 2.45 and 1.34 δ.

EXAMPLE 19

[3-Cyano-3-(2-pyridinyl)propylidene]bisphosphonic acid tetraethyl ester (III)

Ethenylidenebisphosphonic acid tetraethyl ester (I) and 2-pyridinyl acetonitrile (II), NMR (CDCl$_3$) 8.59, 7.72, 7.40, 7.26, 4.63, 4.15, 2.56 and 1.39 δ.

EXAMPLE 20

[4-Cyano-3-(3-pyridinyl)butylidene]bisphosphonic acid tetraethyl ester hemihydrate (III)

Ethenylidenebisphosphonic acid tetraethyl ester (I) and 3-pyridyl acetonitrile (II), MS (m/e) 418, 301, 288 and 131; IR (neat) 2983, 2242, 1582, 1577, 1480, 1444, 1392, 1368 and 1256 cm$^{-1}$; NMR (CDCl$_3$) 8.63, 7.76, 7.36, 4.56, 4.22, 2.48 and 1.37 δ.

EXAMPLE 21

[3-2-Thienyl)-4-nitrilobutylidene]bisphosphonic acid tetraethyl ester (III)

Ethenylidenebisphosphonic acid tetraethyl ester (I) and 2-thiophene acetonitrile (II), IR (neat) 2983, 2242, 1478, 1442 and 1258 cm$^{-1}$; NMR (CDCl$_3$) 7.32, 7.11, 6.99, 4.77, 4.21, 2.54 and 1.36 δ.

EXAMPLE 22

[3-Cyano-3-(2-naphthyl)propylidene]bisphosphonic acid tetraethyl ester (III)

Ethenylidenebisphosphonic acid tetraethyl ester (I) and 2-naphthyl acetonitrile (II), MS (m/e) 467, 288, 181 and 152; NMR (CDCl$_3$) 7.83, 7.42, 4.61, 4.15, 2.50 and 1.32 δ.

EXAMPLE 23

[1-Naphthyl-4-nitrilobutylidene]bisphosphonic acid tetraethyl ester (III)

Ethenylidenebisphosphonic acid tetraethyl ester (I) and 1-naphthyl acetonitrile (II), MS (m/e) 467, 422, 311 and 152; IR (neat) 2983, 2242, 1599, 1541, 1478, 1443 and 1254 cm$^{-1}$; NMR (CDCl$_3$) 8.24, 7.88, 7.74, 7.57, 5.30, 4.20, 2.6 and 1.36 δ.

EXAMPLE 24

[3-Carbomethoxy-3-(1-naphthenyl)-propylidine]bisphosphonic acid tetraethyl ester (III)

Ethenylidenebisphosphonic acid tetraethyl ester (I) and methyl 1-naphthyl acetate (II), MS (m/e) 500, 468, 440 and 288; IR (neat) 2983, 1733, 1597, 1513, 1442, 1368 and 1254 cm$^{-1}$; NMR (CDCl$_3$) 8.26, 7.80, 7.52, 5.06, 4.15, 3.64, 2.71, 2.46 and 1.28 δ.

EXAMPLE 25

[2-(1,2,3,4-Tetrahydro-1-oxo-2-naphtalenylethylidene]-bisphosphonic acid, tetraethyl ester (V)

Ethenylidenebisphosphonic acid tetraethyl ester (I) and tetralone (II), MS (m/e) 446, 301, 288, 261; IR (neat) 3474, 1682, 1253, 1027 and 1026 cm$^{-1}$; NMR (CDCl$_3$) 7.93, 7.40, 7.22, 4.14, 2.96, 2.88, 2.57, 2.21, 1.85 and 1.28 δ.

EXAMPLE 26

(+)-[2-(3,4-Dihydro-4-oxo-2-phenyl-2H-1-benzopyran-3-yl)ethylidene]bisphosphonic acid tetraethyl ester (V)

Ethenylidenebisphosphonic acid tetraethyl ester (I) and flavanone (II), MS (m/e) 524, 479, 302 and 165; IR (neat) 2983, 1683, 1607, 1580, 1499, 1474, 1464 and 1257 cm$^{-1}$.

EXAMPLE 27

[2-(3,4-Dihydro-2-methyl-4-oxo-2H-1-benzothiopyran-3-yl -ethylidene]bisphosphonic acid tetraethyl ester (V)

Ethenylidenebisphosphonic acid tetraethyl ester (I) and 2-methylthiochroman4-one (II), MS (m/e) 478, 462, 432, 302 and 165; IR (neat) 2981, 1675, 1590, 1560, 1478, 1459, 1437, 1391 and 1256 cm$^{-1}$; NMR (CDCl$_3$) 8.04, 7.40, 7.20, 4.17, 3.55, 3.37, 3.10, 2.7–1.9, 1.51 and 1.34 δ.

EXAMPLE 28

[2-(3,4-Dihydro-6-methyl-4-oxo-2H-1-benzothiopyran-3-yl) ethylidene]bisphosphonic acid tetraethyl ester (V)

Ethenylidenebisphosphonic acid tetraethyl ester (I) and 6-methylthiochroman4-one (II), MS (m/e) 478, 302, 288, 191, 177 and 165; IR (neat) 2981, 1674, 1602, 1471, 1443, 1395 and 1253 cm$^{-1}$; NMR (CDCl$_3$) 7.82, 7.13, 4.13, 3.3–3.0, 2.67, 2.26, 1.96 and 1.27 δ.

EXAMPLE 29

[2-(4-Oxo-3,4-dihydro-2H-]-benzopyran-3-yl)ethylidene]bisphosphonic acid tetraethyl ester (V)

Ethenylidenebisphosphonic acid tetraethyl ester (I) and 4-chromanone (II), MS (m/e) 448, 419, 403, 311,302, 288, 165 and 137; IR (neat) 2983, 1689, 1606, 1580, 1480, 1466, 1459 and 1251 cm$^{-1}$; NMR (CDCl$_3$) 7.81, 7.42, 6.93, 4.50, 4.10, 3.20, 2.76, 2.40, 1.87 and 1.28 δ.

EXAMPLE 30

[2-(3-Methyl-2-oxocyclohexyl)ethylidene]bisphosphonic acid tetraethyl ester (VII)

Ethenylidenebisphosphonic acid tetraethyl ester (I) and 2-methyl cyclohexanone (II), MS (m/e) 412, 384, 367, 342, 301 and 288; IR (neat) 2981, 1706, 1477, 1446, 1392, 1368 and 1251 cm$^{-1}$; NMR (CDCl$_3$) 4.19, 3.0–1.5, 1.35 and 1.0 δ.

EXAMPLE 31

[2-(2-Oxo-3-phenylcyclohexyl)ethylidene]bisphosphonic acid tetraethyl ester (VII)

Ethenylidenebisphosphonic acid tetraethyl ester (I) and 2-phenyl cyclohexanone (II), MS (m/e) 474, 429, 418, 301 and 288; IR (neat) 2981, 1708, 1599, 1581, 1491, 1447 and 1250 cm$^{-1}$; NMR (CDCl$_3$) 7.4–7.1, 4.19, 3.85, 3.55, 2.9–1.7, 1.35, 1.83 and 1.11 6; CMR (CDCl$_3$) 212.2, 138.5, 128.7, 127.4, 126.6, 62, 57.1, 39.8, 34.5, 33.2, 31.7, 29.1, 25.4 and 16.1 δ.

EXAMPLE 32

[3-Methoxy4-oxo-4-phenylbutylidene]bisphosphonic acid tetraethyl ester (III)

Ethenylidenebisphosphonic acid tetraethyl ester (I) and 2-methoxy acetophenone (II), MS (m/e) 450, 435, 345, 317, 288, 157 and 105; IR (neat) 2983, 1694, 1598, 1579, 1478, 1448, 1392, 1368, 1252 cm$^{-1}$; NMR (CDCl$_3$) 8.13, 7.60, 7.48, 5.14, 4.15, 3.39, 2.90, 2.30 and 1.35 δ; CDR (CDCl$_3$) 199.0, 134.6, 133.3, 128.4, 128.4, 80, 62.5, 49.4, 32, 28.9, 16.2, 16.1 and 16.0 δ.

EXAMPLE 33

[4-Oxo-4-phenyl-3-phenylthio-butylidene]bisphosphonic acid tetraethyl ester (III)

Ethenylidenebisphosphonic acid tetraethyl ester (I) and α-phenylthio acetophenone (II), MS (m/e) 528,423, 288 and 105; IR (neat) 2982, 1678, 1597, 1570, 1474, 1447, 1439, 1391, 1367 and 1252 cm$^{-1}$; NMR (CDCl$_3$) 7.95, 7.54, 7.43, 7.26, 5.26, 4.16, 2.82, 2.50 and 1.30 δ.

EXAMPLE 34

[4-Oxo-3,4-diphenylbutylidene]-2,2'-methylenebis[5,5-dimethyl-2, 2'-dioxide-1,3,2-dioxaphosphorinane] (III)

2,2'-Ethenylidenebis[5,5-dimethyl-2,2'-dioxide-1,3,2-dioxaphosphorinane] (I, PREPARATION 2) and deoxybenzoin (II), mp 209°–210°; MS (m/e) 520, 416, 371,312 and 105; IR (mineral oil) 1679, 1598, 1581, 1445, 1408, 1277, 1261, 1241 and 1065 cm$^{-1}$; NMR (CDCl$_3$) 7.99, 7.47–7.17, 5.39, 4.33–3.93, 3.76, 3.61, 2.85–2.63, 2.53 –2.37, 1.23, 1.16, 0.99 and 0.84; CMR (CDCl$_3$) 199.2, 138.2, 136.1, 132.6, 128.8, 128.6, 128.3, 128.2, 127.1, 76.7, 50.8, 32.2, 30.4, 28.5, 21.7 and 20.6 δ.

EXAMPLE 35

[3-Benzoylamino4-oxo4-phenylbutylidene]bisphosphonic acid tetraethyl ester (III)

Ethenylidenebisphosphonic acid tetraethyl ester (I) and N-phenacylbenzamide (II), MS (m/e) 539, 434 and 388; IR (neat) 3280, 2982, 1691, 1657, 1598, 1580, 1537, 1491, 1448, 1392, 1368 and 1251 cm$^{-1}$; NMR (CDCl$_3$) 8.21, 7.98, 7.61, 7.48, 5.95, 4.27, 4.10, 2.82, 2.57, 2.36, 1.34 and 1.23 δ.

EXAMPLE 36

[3-t-Butoxycarbonylamino-4-oxo4-phenylbutylidene]-bisphosphonic acid tetraethyl ester (III)

Ethenylidenebisphosphonic acid tetraethyl ester (I) and 2-(3-t-butoxycarbonylaminoacetophenone) (II), mp 56°–57°; MS (m/e) 535,462, 374, 330 and 284; IR (mineral oil) 3271, 1712, 1691, 1598, 1580 and 1251 cm$^{-1}$; NMR (CDCl$_3$) 8.18, 7.60, 7.47,58, 4.27, 4.12, 2.75, 2.42, 1.96, 1.42 and 1.31 δ.

EXAMPLE 37 cis-[2-(3,4-Dihydro-4-oxo-2-phenyl-2H-1-benzopyran-3yl) ethylidene]bisphosphonic acid tetraethyl ester (V)

Upon standing a precipitate appeared in [2-(3,4-dihydro4-oxo-2-phenyl-2H-1-benzopyran-3-yl)ethylidene]-bisphosphonic acid tetraethyl ester (V, EXAMPLE 26). This solid is separated and recrystallized from ether to give the cis isomer, NMR (CDCl$_3$) 7.93, 7.45, 7.08, 5.65, 4.00, 3.32, 2.59, 2.02, 1.20, 1.09 and 1.03 δ; CMR (CDCl$_3$) 194.9, 160.7, 136.3, 135.9, 128.4, 127.9, 127.4, 126.7, 121.7, 119.4, 117.8, 80.9, 62.5, 62.4, 62.2, 49.6, 49.2, 32, 19.8, 16.12, 15.9, 15.8 and 15.7 δ.

EXAMPLE 38 trans-[2-(3,4-Dihydro4-oxo-2-phenyl-2H-1-benzopyran-3-yl)ethylidene]bisphosphonic acid tetraethyl ester (V)

The mother liquor from EXAMPLES 26 and 37 is nearly pure trans isomer, NMR (CDCl$_3$) 7.77, 7.35, 6.91, 5.09, 3.95, 2.90, 2.26 and 1.61 δ.

EXAMPLE 39

[3-(4-Methoxybenzoyl)-3-(2-pyridinyl)propylidene]bisphosphonic acid tetraethyl ester (III)

N-butyl lithium (1.6M in hexane, 62.5 ml) is added slowly to a solution of 2-picoline (9.9 ml) in ether (100 ml). The refluxing reaction is stirred for 30 min, then a solution of methyl 4-methoxy benzoate (8.31 g) in ether (50 ml) is added slowly so that the reflux is maintained. After maintaining the reflux for an additional 30 min, the reaction is poured on to ice/hydrochloric acid, diluted with ethyl acetate, and extracted with hydrochloric acid (10%, 3×). The acidic fractions are backwashed with ethyl acetate then neutralized with sodium hydroxide and sodium bicarbonate until the pH is 7.5. The product is extracted into ethyl acetate, dried with magnesium sulfate, and concentrated under reduced pressure. The product is distilled bp$_{0.2}$ 175°–185°, then the solidified product is recrystallized from cyclohexane, to give 1-(4-methoxyphenyl)-2-(2-pyridinyl)ethanone (II).

Ethenylidenebisphosphonic acid tetraethyl ester (I, 3.00 g), 1-(4-methoxyphenyl)-2-(2-pyridinyl)ethanone (II, 2.50 g) and potassium carbonate (2.07 g) are stirred in methanol (20 ml) overnight. The reaction is concentrated under reduced pressure, taken up in ethyl acetate, washed with sodium chloride, dried with magnesium sulfate, rand concentrated under reduced pressure. The product is chromatographed eluting with ethyl acetate, ethyl acetate/acetone (1/1), acetone, the appropriate fractions are pooled and concentrated to give the title compound, MS (m/e) 527 and 240; IR (neat) 2982, 1674, 1499, 1475, 1470, 1435, 1321, 1392 and 1253 cm$^{-1}$; NMR (CDCl$_3$) 8.53, 8.02, 7.61, 7.35, 7.12, 6.85, 5.41, 4.16, 3.81, 2.77, 2.50, 1.38, 1.26 and 1.17 δ; CMR (CDCl$_3$) 196.5, 163.2, 158.8, 149.7, 136.7, 131.1, 129.3, 122.8, 121.9, 113.5, 62.8, 62.7, 62.4, 62.3, 62.2, 55.2, 53.5, 33.9, 28.4, 16.3, 16.2, 16.1 and 16.0 δ.

EXAMPLE 40

[4-Oxo4-phenyl-3-(2-pyridinyl)butylidene]bisphosphonic acid tetraethyl ester hemihydrate (HI)

n-Butyl lithium (1.6M in hexane, 62.5 ml) is added slowly to a solution of 2-picoline (9.9 ml, 0.10 mol) in ether (100ml). The refluxing reaction is stirred for 30 min, then a solution of methyl benzoate (6.25 ml) in ether (10 ml) is added slowly so that the reflux is maintained. After maintaining the reflux for an additional 30 min, the reaction is poured on to ice/hydrochloric acid, diluted with ethyl acetate, and extracted with hydrochloric acid (10%, 3×). The acidic fractions are back-washed with ethyl acetate then neutralized with sodium hydroxide and sodium bicarbonate until the pH is 7.5. The product is extracted into ethyl acetate, dried with magnesium sulfate, and concentrated under reduced pressure. The product is distilled to give 1-phenyl-2-(2-pyridinyl)ethanone (II).

Ethenylidenebisphosphonic acid tetraethyl ester (I, 3.00 g), 1-phenyl-2-(2-pyridinyl)ethanone (II, 2.17 g) and potassium carbonate (2.07 g) are stirred in methanol (20 ml) overnight. The reaction is concentrated under reduced pressure, taken up in ethyl acetate, washed with sodium chloride, dried with magnesium sulfate, and concentrated under reduced pressure. The product is chromatographed eluting with ethyl acetate. The appropriate fractions are pooled and concentrated to give the title compound, MS (m/e) 497, 452, 392, 302 and 288; IR (neat) 2983, 1683, 1597, 1580, 1470, 1448 and 1253 cm$^{-1}$; NMR (CDCl$_3$) 8.52, 8.02, 7.60, 7.49, 7.37, 7.11, 5.46, 4.12, 2.75, 2.55, 1.36, 1.25 and 1.16 δ.

EXAMPLE 41

[4-(3'-Fluorophenyl)4-oxo-butylidene]bisphosphonic acid tetraethyl ester (III)

3'-Fluoroacetophenone (II, 0.84 ml) is dissolved in THF (23ml) and cooled to −78° and is treated with lithium hexamethyldisilazane (LiHMDS, 7.5 ml) and stirred for 30 minutes. A solution of ethylidenebisphosphonic acid tetraethyl ester (I, 1.87g) in THF (7 ml) is added, stirred 10 minutes then warmed to 0° for 1 hour. The mixture is quenched with saturated ammonium chloride and then the solvents are removed under reduced pressure and mild heat. The residue is diluted with ethyl acetate and washed with saturated sodium bicarbonate (3×) saline, dried with magnesium sulfate and the solvents removed under reduced pressure with mild heat. The concentrate is chromatographed eluting with alcohol/ethyl acetate (5/95). The appropriate fractions are pooled and concentrated to give the title compound, MS (m/e) 439 (M+), 435, 411, 393, 301 and 123; IR (neat) 1689, 1588, 1483, 1444, 1392, 1368, 1250 and 1164 cm$^{-1}$; NMR (CDCl$_3$) 7.76, 7.65, 7.48–7.35, 7.26, 4.18, 3.37, 2.58, 2.41–2.27 and 1.33 δ; CMR (CDCl$_3$) 197.9, 133.8, 130.3, 126.8, 123.8, 120.1, 114.7, 62.6, 37.1, 35.5, 20.2 and 16.4 δ.

EXAMPLE 42

[4-(4'-Ethoxycarbonylaminophenyl)4-oxo-butylidene]bisphosphonic acid tetraethyl ester (III)

4-Amino acetophenone (4.06 g), ethyl chloroform ate (3.0 ml), and potassium carbonate (4.20 g) are heated in refluxing toluene (30 ml) for 4 hours, then cooled, filtered and washed with boiling water. The pure material is obtained by recrystallizing from toluene to give 4-ethoxycarbonylaminoacetophenone (II).

The 4-ethoxycarbonylaminoacetophenone (II, 1.865 g) in pyridine (25 ml) at 0° is treated with LiHMIDS (1M in THF, 19.0 ml) and stirred at 22° for 30 min. Ethenylidenebisphosphonic acid tetraethyl ester (I, 2.70 g) is added and stirring maintained for 30 min. The reaction is poured onto hydrochloric acid (10%), extracted fluid with methylene chloride, washed with 10% hydrochloric acid, sodium chloride, dried with magnesium sulfate and concentrated under reduced pressure with mild heat. Pure material is obtained by chromatography eluting with ethyl acetate, ethyl acetate/acetone (1/1) and recrystallization from ethyl acetate to give the title compound, mp 96–97; MS (m/e) 507, 462, 380, 3 15, 288 and 192.

EXAMPLE 43

[4-(4'-Acetamidophenyl)4-oxo-butylidene]bisphosphonic acid tetraethyl ester (III)

4-Aminoacetophenone (2.42 g), acetyl chloride (1.5 ml), and triethylamine (3.5 ml) are stirred in THF (40 ml) at 22°. After 4 hours, the reaction is quenched with 10% hydrochloric acid, extracted thrice with methylene chloride, washed with hydrochloric acid (1N) and sodium chloride, dried with magnesium sulfate, and concentrated under reduced pressure with mild heat. The product is recrystallized from water to give 4-acetamidoacetophenone (II).

The 4-acetamidoacetophenone (II, 1.60 g) in pyridine (25 ml) at 0° is treated with LiHMDS (1M in THF, 19.0 ml) and stirred at 22° for 30 min. Ethenylidenebisphosphonic acid tetraethyl ester (I, 2.70 g) is added and the stirring continued for 30 min. The reaction is poured onto 10% hydrochloric acid, extracted thrice with methylene chloride, washed with hydrochloric acid (1N), dried with magnesium sulfate, and concentrated under reduced pressure with mild heat. The concentrate is chromatographed eluting with ethyl acetate, ethyl acetate/acetone (1/1), then recrystallized from ethyl acetate to give the title compound, mp 96°–97°; MS (m/e) 477, 432, 340 315, 301, 288 and 162.

EXAMPLE 44

[1-Methyl-4-oxo-4-phenylbutylidene]bisphosphonic acid tetraethyl ester (III)

(4-Oxo-4-phenylbutylidene)bisphosphonic acid tetraethyl ester (III, EXAMPLE 47, 840 mg) is dissolved in THF (1.0 ml) and cooled to −78 C. Lithium hexamethyldisilazane (1M in THF, 2.3 ml) is added and the reaction stirred for 1 hour at −78°. Methyl iodide (0.5 ml) is added and the reaction is warmed to 22°. After stirring for 40 min, the reaction is quenched with hydrochloric acid (1N) and ethyl acetate, washed twice each with hydrochloric acid (1N), sodium bicarbonate, and saline, dried with magnesium sulfate and concentrated under reduced pressure with mild heat. The crude material is purified by column chromatography eluting with ethyl acetate, ethyl acetate/acetone (3/7). The appropriate fractions are pooled and concentrated to give the title compound, MS (m/e) 434, 406, 389, 302, 297, 165 and 105.

EXAMPLE 45

[4-(4'-Hydroxyphenyl)-4-oxo-butylidene]bisphosphonic acid tetraethyl ester (III)

4'-Hydroxyacetophenone (1.16 g) dissolved in toluene (40 ml) is treated with a strongly acidic ion exchange resin (50 mg) and the solvent is distilled until no water remains. Hexamethyldisilazane (5 ml) is added and the solution is heated to reflux for 24 hours. The mixture is filtered and concentrated under reduced pressure with mild heat to give 4'-trimethylsilyloxyacetophenone.

4'-Trimethylsilyloxyacetophenone (II, 1.65 g) dissolved in THF (26 ml) and cooled to −78° is treated with LiHMDS (8.7 ml) and stirred for 30 minutes. A solution of ethenylidenebisphosphonic acid tetraethyl ester (I, 2.17 g) in THF (5 ml) is added, stirred 30 minutes then warmed to 0° for 2 hours. The mixture is quenched with hydrochloric acid (6N, 20 ml) and stirred for 1 hour at 0°. The mixture is neutralized with sodium hydroxide and concentrated under reduced pressure with mild heat. The concentrate is diluted with ethyl acetate and washed with saturated sodium bicarbonate (3×), saline, dried with magnesium sulfate and concentrated with reduced pressure and mild heat. The concentrate is chromatographed eluting with ethyl acetate. The appropriate fractions are pooled and concentrated to give the title compound, MS (m/e) 43, 391, 363, 315, 299, 288, 261, 233, 205, 179, 152 and 121; IR (neat) 3148, 1672, 1604, 1584, 1515, 1443, 1391, 1369, 1244 and 1220 cm$^{-1}$; CMR (CDCl$_3$) 197, 162, 130, 128, 115, 63, 36, 35.2, 20 and 16 $\delta$.

EXAMPLE 46

[4-(2'-Hydroxyphenyl)-4-oxo-butylidene]bisphosphonic acid tetraethyl ester (III)

2'-Hydroxyacetophenone (1.89 g) dissolved in toluene (65 ml) is treated with a strongly acid ion exchange resin (50 mg) and the solvent is distilled until no water remains. Hexamethyldisilazane (8.5 ml) is added and the solution is heated to reflux for 48 hours. The mixture is filtered and concentrated under reduced pressure with mild heat to give 2'-trimethylsilyloxyacetophenone.

2'-Trimethylsilyloxyacetophenone (II, 2.89 g) is dissolved in THF (45 ml) and cooled to −78° and then treated with LiHMDS (15.3 ml) and stirred for 30 minutes. A solution of ethenylidenebisphosphonic acid tetraethyl ester (I, 3.79 g) in THF (5 ml) is added, stirred for 30 minutes then warmed to 0° for 1 hour. The reaction mixture is quenched with saturated ammonium chloride and concentrated under reduced pressure with mild heat. The concentrate is diluted with ethyl acetate and washed with hydrochloric acid (1N), water, saturated sodium bicarbonate, saline, dried with magnesium sulfate and concentrated under reduced pressure with mild heat. The concentrate is chromatographed eluting with ethyl acetate. The appropriate fractions are pooled and concentrated to give the title compound, MS (m/e) 436, 391, 315, 301, 299, 288, 152 and 121; CMR (CDCl$_3$) 205, 162, 136, 130, 119.2, 119, 118.5, 62, 36.6, 35.6, 20 and 16.4 $\delta$.

EXAMPLES 47-64

Following the general procedure of EXAMPLES 41-46 using LiHMDS in THF as the base and making non-critical variations but starting with the appropriate electron deficient olefin (I) and activated methylene (II), the title compounds are obtained.

EXAMPLE 47

(4-Oxo4-phenylbutylidene)bisphosphonic acid tetraethyl ester (III)

Ethenylidenebisphosphonic acid tetraethyl ester (I) and acetophenone (II), MS (m/e) 420, 375, 315, 301,287 and 283; IR (neat) 1684, 1597, 1581, 1449, 1392, 1369, 1251 and 1164 cm$^{-1}$; NMR (CDCl$_3$) 7.97, 7.56, 7.45, 4.18, 3.39, 2.60, 2.33 and 1.30 $\delta$.

EXAMPLE 48

[5,5-Dimethyl-4-oxo-hexylidene]bisphosphonic acid tetraethyl ester (III)

Ethenylidenebisphosphonic acid tetraethyl ester (I) and pinacolone (II), MS (m/e) 343, 315, 301,287, 259, 231 and 213; IR (neat) 1704, 1479, 1466, 1457, 1444, 1253, 1164 and 1027 cm$^{-1}$; CMR (CDCl$_3$) 215.2, 62.5, 43.9, 35.6, 35.0, 26.4, 20 and 16.4 $\delta$.

EXAMPLE 49

[4-(4'-Morpholinophenyl)-4-oxo-butylidene]bisphosphonic acid tetraethyl ester (III)

Ethenylidenebisphosphonic acid tetraethyl ester (I) and 4-morpholinoacetophenone (II, 0.94 g), MS (m/e) 505, 368, 315, 301, 288, 261, 218, 205 and 190; CMR (CDCl$_3$) 197.5, 154, 130, 127.7, 113.3, 66.6, 62, 47.5, 36.3, 36.7, 20.5 and 16.4 $\delta$.

EXAMPLE 50

[4-Oxo-pentylidene]bisphosphonic acid tetraethyl ester (III)

Ethenylidenebisphosphonic acid tetraethyl ester (I) and acetone (II), MS (m/e) 358, 316, 301, 288, 261, 233, 221, 179 and 152; CMR (CDCl$_3$) 207.5, 62.4, 41.4, 34.8, 19.4 and 16 $\delta$.

EXAMPLE 51

[4-(4'-Methylphenyl)4-oxo-butylidene]bisphosphonic acid tetraethyl ester (Ill)

Ethenylidenebisphosphonic acid tetraethyl ester (I) and 4'-methylacetophenone (II), MS (m/e) 434, 389, 315, 301,297, 288 and 119; CMR (CDCl$_3$) 199.5, 143.5, 134, 128.9, 127.8, 62.3, 36.3, 35.2, 21.3, 20 and 16 $\delta$.

EXAMPLE 52

[4-(4'-Methoxyphenyl)4-oxo-butylidene]bisphosphonic acid tetraethyl ester (III)

Ethenylidenebisphosphonic acid tetraethyl ester (I) and 4'-methoxyacetophenone (II, 0.75 g), MS (m/e) 450, 315, 313, 301, 288 and 135; IR (neat) 1676, 1600, 1576, 1512, 1443, 1419, 1392, 1369, 1255 and 1171; NMR (CDCl$_3$) 7.96, 6.92, 4.18, 3.69, 3.33, 2.61, 2.34 and 1.33 $\delta$; CMR (CDCl$_3$) 197.6, 163.3, 130, 129.7, 113.5, 62.5, 55.3, 36.2, 35.3, 20.2 and 16.2 $\delta$.

EXAMPLE 53

[4-Oxo4-(3-pyridinyl)-butylidene]bisphosphonic acid tetraethyl ester (III)

Ethenylidenebisphosphonic acid tetraethyl ester (I) and 3-acetylpyridine (II, 0.77 ml); MS (m/e) 421, 376, 315, 301, 283, 273, 261, 152 and 106; IR (neat) 1690, 1585, 1572, 1478, 1443, 1419, 1393, 1369, 1251 and 1164 cm$^{-1}$; NMR (CDCl$_3$) 9.18, 8.77, 8.25, 7.42, 4.2, 3.41, 2.59, 2.38 and 1.33 δ; CMR (CDCl₃) 498, 154, 149, 136, 132, 124, 63, 38, 36(t), 20 and 16 δ.

EXAMPLE 54

[4-Oxo-4-(2-thiophenyl)-butylidene]bisphosphonic acid tetraethyl ester

Ethenylidenebisphosphonic acid tetraethyl ester (I), and 2-acetylthiophene (II, 0.76 ml); MS (m/e) 426, 381, 315, 289, 261, 152 and 111; IR (neat) 1663, 1518, 1478, 1443, 1416, 1392, 1368, 1355, 1250, 1164 and 1142 cm⁻¹; NMR (CDCl₃) 7.77, 7.62, 7.12, 4.2, 3.32, 2.58, 2.36 and 1.33 67 ; CMR (CDCl₃) 192, 144, 133.5, 135.5, 128, 62, 38, 32.5 (t), 20.5 and 16 δ.

EXAMPLE 55

[4-Oxo-4-phenylbutylidene]-2,2'-methylenebis[5,5-dimethyl-2,2'-dioxide 1,3,2-dioxaphosphorinane] (III)

2,2'-Ethenylidenebis[5,5-dimethyl-2,2'-dioxide-1,3,2,-dioxaphosphorinane] (I, PREPARATION 1) and acetophenone (II, 0.58 ml), mp 199°-200°; MS (m/e) 444, 339, 325, 312, 295 and 105.

EXAMPLE 56

[4-Oxo4-(2',3',4'-trichlorophenyl)-butylidene]bisphosphonic acid tetraethyl ester (III)

Ethenylidenebisphosphonic acid tetraethyl ester (I) and 2,3,4-trichloracetophenone (II, 1.12 g); MS (m/e) 522, 487, 385, 315, 301,288 and 207; IR (neat) 1707, 1572, 1442, 1392, 1366, 1253 and 1170 cm⁻¹; NMR (CDCl₃) 7.45, 7.35, 4.20, 3.31, 2.53, 2.34 and 1.35 δ; CMR (CDCl₃) 200, 139, 136, 132.7, 130.5, 128, 126, 62, 40.9, 35.1, 19.8 and 16 δ.

EXAMPLE 57

[4-(3',5'-Difluorophenyl)4-oxo-butylidene]bisphosphonic acid tetraethyl ester (III)

Ethenylidenebisphosphonic acid tetraethyl ester (I) and 3',5'-difluoroacetophenone (II, 0.96 g); MS (m/)e 456, 428, 411, 319, 301, 288 and 141; IR (neat) 1694, 1619, 1441, 1392, 1369, 1252, 1164, 1122 cm⁻¹; NMR (CDCl₃) 7.48, 7.02, 4.20, 3.35, 2.56, 2.35 and 1.34 δ; CMR (CDCl₃) 196.4, 162.8, 163.1, 139.4, 110.6, 108.1, 62.4, 36.8, 35.2, 19.9 and 16.1 δ.

EXAMPLE 58

[4-(4'-Chlorophenyl)4-oxo-butylidene]bisphosphonic acid tetraethyl ester (III)

Ethenylidenebisphosphonic acid tetraethyl ester (I) and 4'-chloroacetophenone (II, 0.65 ml); MS (m/e) 454, 409, 317, 315, 301, 288, 243 and 139; IR (neat) 1685, 1589, 1572, 1488, 1443, 1397, 1252 and 1164 cm⁻¹; NMR (CDCl₃) 7.94, 7.43, 4.19, 3.37, 2.59, 2.38 and 1.34 δ; CMR (CDCl₃) 197.6, 139.2, 134.7, 129.1, 128.6, 62.3, 36.6, 35.1, 19.9 and 16.1 δ.

EXAMPLE 59

[3,3-Dimethyl-4-oxo-4-phenylbutylidene]bisphosphonic acid tetraethyl ester (III)

Ethenylidenebisphosphonic acid tetraethyl ester (I) and isobutyrophenone (II, 1.35 ml); MS (m/e) 448, 403, 343, 301, 287, 243 and 105; IR (neat) 1674, 1639, 1597, 1473, 1460, 1392, and 1252 cm⁻¹; NMR (CDCl₃) 7.57, 7.44, 4.12, 2.57, 2.53, 1.33 and 1.28 δ.

EXAMPLE 60

[4-(3',4'-Dichlorophenyl)4-oxo-butylidene]bisphosphonic acid tetraethyl ester (III)

Ethenylidenebisphosphonic acid tetraethyl ester (I) and 3',4'-dichloroacetophenone (II, 0.94 g); MS (m/e) 489, 443, 351, 315, 301, 288 and 173; IR (neat) 1690, 1584, 1556, 1391 and 1252 cm⁻¹; NMR (CDCl₃) 8.05, 7.81, 7.54, 4.19, 3.36, 2.56, 2.34 and 1.34 δ; CMR (ICDCl₃) 196.9, 137.6, 136.2, 133.3, 130.7, 130, 127, 62.6, 37, 35.4, 20.1 and 16.4 δ.

EXAMPLE 61

[4-Oxo-4-(4-pyridinyl)-butylidene]bisphosphonic acid tetraethyl ester (III)

Ethenylidenebisphosphonic acid tetraethyl ester (I) and 4-acetylpyridine (II, 1.0 ml); MS (m/e) 421, 393, 376, 315, 301, 288, 284, 106 and 78; IR (neat) 3478,1697, 1593, 1556, 1443, 1408, 1392, 1369, 1252 and 1164 cm⁻¹; NMR (CDCl₃) 8.81, 7.77, 4.17, 3.41, 2.76–2.55, 2.52–2.28 and 1.34 δ; CMR (CDCl₃) 198.6, 150.8, 142.6, 121.0, 62.8–62.2, 37.2–36.8, 35.3, 19.9 and 16.4 δ.

EXAMPLE 62

[4-Oxo-4-(2-furanyl)-butylidene]bisphosphonic acid tetraethyl ester (III)

Ethenylidenebisphosphonic acid tetraethyl ester (I) and 2-acetylfuran (II, 0.77 g); MS (m/e) 410, 365, 315, 301, 288, 273 and 95; IR (neat) 1676, 1570, 1470, 1394, 1369, 1252 and 1164 cm⁻¹; NMR (CDCl₃) 7.58, 7.22, 6.53, 4.20, 3.23, 2.56, 2.42–2.24 and 1.33 δ; CMR (CDCl₃) 188, 153, 146.3, 117.1, 112.2, 62.6, 36.6, 35.5 (t), 20 and 16.4 δ.

EXAMPLE 63

[1-Chloro4-oxo4-phenylbutylidene]bisphosphonic acid tetraethyl ester (III)

Acetophenone (1.17 ml) is dissolved in THF (20 ml), cooled to −78° and treated with lithium bis(trimethylsilyl)amide. The solution is stirred for 30 minutes and a solution of ethenylidenebisphosphonic acid tetraethyl ester (I, 2.7g) in THF (5 ml) is added. The solution is stirred for several minutes then warmed to 0° for 1 hour. N-Chlorosuccinimide (1.33 g) is added and the solution was stirred at 22° for 18 hours. The reaction is quenched with aqueous ammonium chloride and concentrated. The residue is diluted with ethyl acetate and washed with sulfuric acid (2N, 2×), water, sodium bicarbonate, saline and dried with magnesium sulfate and concentrated. The resultant mixture is chromatographed eluting with ethyl acetate, slowly increased from 1 to 5% ethanol/ethyl acetate. The appropriate fractions are pooled and concentrated to give the title compound, MS (m/e) 454, 426, 322 and 105; IR (neat) 1686, 1599, 1581, 1448, 1391, 1368, 1259, 1214 and 1163 cm⁻¹; NMR (CDCl₃) 8.02–7.99, 7.59–7.54, 7.49–7.44, 4.37–4.25, 3.50, 2.78–2.64 and 1.38 δ. Another compound is formed by the reaction which is not within the scope of the invention.

EXAMPLE 64

[4-Oxo-6-phenyl-hex-5-en-ylidene]bisphosphonic acid tetraethyl ester (III)

Ethenylidenebisphosphonic acid tetraethyl ester (I) and freshly distilled 4-phenyl-3-buten-2-one (II, 1.61 g); MS (m/e) 446, 401, 288, 131 and 103; IR (neat) 1712, 1690, 1662, 1612, 1576, 1495, 1450, 1391, 1369 and 1252 cm$^{-1}$; NMR, (CDCl$_3$) 7.58, 7.53, 7.39, 6.73, 4.19, 3.09, 2.54, 2.29 and 1.34 δ; CMR (CDCl$_3$) 199, 142, 135, 130, 129, 129, 126, 62, 39, 36, 20 and 16.4 δ.

EXAMPLE 65

[4-(2'-Benzamidophenyl)-4-oxo-butylidene]bisphosphonic acid tetraethyl ester (III)

2-Amino acetophenone (4.05 g) and benzoyl chloride (4.0 ml) in methylene chloride (50 ml) at 0° are treated with triethylamine (5.5 ml), warmed to 220 and stirred for 1 hour. The reaction is treated with hydrochloric acid (1N) and the solvents removed by reduced pressure with mild heat to remove most of the THF. The product is isolated by filtration and purified by recrystallization from methanol to give 2-benzamideacetophenone (II). The benzamide (II, 1.67 g) is dissolved in pyridine (15 ml) at 0°, treated with LiHMIDS (1M in THF, 15.0 ml) and stirred at 22° for 30 min. Ethenylidenebisphosphonic acid tetraethyl ester (I, 2.10 g) is added and the reaction stirred for 1 hour. It is poured onto 10% hydrochloric acid, extracted thrice with methylene chloride, washed with saline, dried with magnesium sulfate and concentrated under reduced pressure. The concentrate is purified by chromatography eluting with ethyl acetate, ethyl acetate/acetone (1/1) then recrystallization from methyl t-butyl ether to give the title compound, mp 100°; MS: m/e 539, 521, 434, 417, 402, 315, 301, 288, 224, 105; IR (mineral oil) 3223, 1674, 1655, 1608, 1587, 1538, 1449 and 1246 (cm$^{-1}$); NMR (CDCl$_3$) 12.7, 8.97, 8.06, 7.56, 7.16, 4.20, 3.49, 2.56, 2.40 and 1.34 δ.

EXAMPLE 66

[4-(3'-Ethoxycarbonylaminophenyl)4-oxo-butylidene]-bisphosphonic acid tetraethyl ester (III)

3-Amino acetophenone (4.05 g) in pyridine (6 ml) at 0° is treated dropwise with a solution of ethyl chloroformate (3.3 mml) in ether (15 ml). The reaction is stirred for 1 hour, diluted with water, filtered, the solid recrystallized from toluene to give the carbamate, 3-ethoxycarbonylaminoacetophenone (II)

The carbamate (11, 1.45 g) is dissolved in pyridine (15 ml) at 0° and treated with LiHMDS (15.0 ml). After stirring at 22° for 30 min, ethenylidenebisphosphonic acid tetraethyl ester (I, 2.1 g) is added and stirring maintained for I more hour. The mixture is poured onto hydrochloric acid (10%), extracted thrice with methylene chloride, dried with magnesium sulfate, the solvents removed under reduced pressure with mild heat the concentrate is chromatographed eluting with ethyl acetate, ethyl acetate/acetone (3/7). The appropriate fractions are pooled and concentrated. The concentrate is triturated with toluene to give the title compound, mp 83°-84°; MS (m/e) 507, 462, 435, 370 and 288; IR (mineral oil) 3252, 1734, 1686, 1598, 1557, 1482 and 1247 cm$^{-1}$; NMR (CDCl$_3$) 8.02, 7.97, 7.75, 7.60, 7.33, 4.20, 3.37, 2.64, 2.40 and 1.30 δ.

EXAMPLE 67

[4-(4'-(4-Chlorobenzamido)phenyl)4-oxo-butylidene]-bisphosphonic acid tetraethyl ester (III)

4-Aminoacetophenone (3.88 g) and 4-chlorobenzoyl chloride (4.00 ml) are cooled in methylene chloride (50 ml) to 0°, and treated with triethylamine (5.00 ml). The reaction is stirred at 22° for 30 min, then poured onto 10% hydrochloric acid. The slurry is stirred for 15 min then filtered. The precipitate is recrystallized from acetone to give the benzamide, 4-(4-chlorobenzamido)acetophenone (II).

The benzamide (II, 1.37 g) is dissolved in pyridine (5.0 ml), cooled to 0°, and treated with LiHMDS (1M in THF, 11 ml). The mixture is stirred for 30 min, whereupon ethenylidenebisphosphonic acid tetraethyl ester (I, 1.50 g) is added. After stirring at 22° for 1 hour, the mixture is poured onto 10% hydrochloric acid and stirred for 6 hours. The solid is collected. The solid is dissolved in ethanol, treated with charcoal, filtered through celite and the solvents are removed by reduced pressure with mild heat to give a solid. The solid is recrystallized from ethanol, methyl t-butyl ether to give the title compound, mp 130°-131°; MS (m/e) 573, 436, 288 and 139; IR (mineral oil) 3304, 3191, 1678, 1665, 1599, 1533, 1491 and 1263 cm$^{-1}$; NMR (CDCl$_3$) 8.63, 7.94, 7.80, 7.46, 4.17, 3.33, 2.60, 2.36 and 1.32 δ.

EXAMPLE 68

[4-(3'-(4-Nitrobenzamido)phenyl)4-oxo-butylidene]bisphosphonic acid tetraethyl ester (III)

3-Aminoacetophenone (4.05 g) and 4-nitrobenzoyl chloride (5.75 g) are cooled in methylene chloride (50 ml) to 0°, and treated with triethylamine (5.00 ml). The reaction is stirred at 22° for 30 min, then poured onto hydrochloric acid (10%). The slurry is stirred for 1 hour then filtered. The precipitate is recrystallized from DMF/water to give a benzamide, 3-(nitobenzamido)acetophenone (II).

The benzamide (II, 1.99 g) is dissolved in pyridine (15.0 ml), cooled to 0°, and treated with LiHMDS (1M in THF, 14 ml). The suspension is stirred for 30 min, whereupon ethenylidenebisphosphonic acid tetraethyl ester (I, 2.10 g) is added. After stirring at 22° for 1 hour, it is poured onto hydrochloric acid (10%), extracted thrice with methylene chloride, dried with magnesium sulfate, and concentrated with reduced pressure and mild heat. The concentrate is chromatographed eluting with ethyl acetate, ethyl acetate/acetone (3/7), the appropriate fractions are pooled and concentrated. The concentrate is then recrystallized from acetone to give the title compound, mp 111°-112°; MS (m/e) 584, 462, 448, 429, 332, 315, 301 and 288; IR (mineral oil) 3106, 1684, 1672, 1600, 1553, 1521, 1485 and 1256 cm$^{-1}$; NMR (CDCl$_3$) 8.32, 8.21, 7.70, 7.44, 4.15, 3.36, 2.67, 2.36 and 1.31 δ.

EXAMPLE 69

[4-(4'-Benzamidophenyl)4-oxo-butylidene]bisphosphonic acid tetraethyl ester (III)

The 4-benzamidoacetopehenone (11, 3.13 g) is dissolved in pyridine (25 ml), cooled to 0°, and treated slowly with LiHMDS (1.0M in THF, 28 ml). The reaction is stirred at 0° for 30 min, then treated with ethenylidenebisphosphonic acid tetraethyl ester (I, 3.924 g). After stirring at 0° for 30 min and 30 min at 22°, the reaction is poured onto hydrochloric acid (10%), and extracted with ethyl acetate. The combined organics are washed with hydrochloric acid (1N) and saline, treated with charcoal, filtered through a pad of magnesium sulfate and concentrated under reduced pressure with mild heat. The concentrate is recrystallized from ethyl acetate to give the title compound, mp 110°-112°; IR (mineral oil) 3315, 1666, 1596, 1535, 1258 cm$^{-1}$; NMR (CDCl$_3$)8.57, 7.97, 7.91, 7.80, 7.53, 4.17, 3.34, 2.60, 2.3 and 1.31 δ.

EXAMPLE 70

[4-Hydroxy4-phenylbutylidene]bisphosphonic acid tetraethyl ester (III)

(4-Oxo4-phenylbutylidene)bisphosphonic acid tetraethyl ester (III, EXAMPLE 47, 1.80 g) is dissolved in THF/water (7/1, 8 ml), treated with sodium borohydride (150 mg) and stirred at 22° for 1 hour. The reaction is carefully acidified, extracted thrice with ethyl acetate, washed with sodium bicarbonate, dried with magnesium sulfate, and concentrated. The concentrate is chromatographed eluting with ethyl acetate, the appropriate fractions are pooled and concentrated to give the title compound, MS (m/e) 422, 404, 376, 316, 302, 288, 179 and 165; IR (neat) 3388, 2981, 1492, 1478, 1392 and 1249 cm$^{-1}$; NMR (CDCl$_3$) 7.28, 4.68, 4.12, 3.46, 2.41, 4.7, 2.02 and 1.31 δ.

EXAMPLE 71

[4-Hydroxy-3,4-diphenylbutylidene]bisphosphonic acid tetraethyl ester (III)

Following the general procedure of EXAMPLE 70 and making non-critical variations but starting with (4-oxo-3,4-diphenylbutylidene)bisphosphonic acid tetraethyl ester (III, EXAMPLE 11, 1.00 g), the title compound is obtained; MS (m/e) 498, 480, 453, 392 and 288; IR (neat) 3380, 2982, 1602, 1494, 1453 and 1249 cm$^{-1}$; NMR (CDCl$_3$) 7.28, 4.75, 4.00, 3.46, 2.1 and 1.25 δ.

EXAMPLE 72

[1,3,3-Trichloro-4-oxo4-phenylbutylidene]bisphosphonic acid tetraethyl ester (III)

(4-Oxo-4-phenylbutylidene)bisphosphonic acid tetraethyl ester (III, EXAMPLE 47, 0.9 15g) is treated with solid sodium bicarbonate (2.62g) and cold sodium hypochlorite solution (11.5 ml) and stirred at 0° for 2 hours and warmed to 22° for 5 days. The mixture is diluted with ethyl acetate and washed twice with sodium bicarbonate, saline, dried with magnesium sulfate and concentrated. The concentrate is chromatographed eluting with ethyl acetate. The appropriate fractions are pooled and concentrated to give the title compound, NMR (CDCl$_3$) 8.11–8.04, 7.61–7.42, 5.93, 4.34–4.17, 3.88–3.78, 2.81 and 1.42–1.31 δ.

EXAMPLE 73

(4-Oxo-3,4-diphenylbutylidene)bisphosphonic acid diethylester disodium salt (III)

(4-Oxo-3,4-diphenylbutylidene)bisphosphonic acid tetraethyl ester (III, EXAMPLE 11, 3.77 g) and sodium iodide (2.28 g) are heated in refluxing methyl ethyl ketone (10 ml) for 18 hours. After 2 hours a slight cloudiness develops in the reaction, and after 4 hours the reaction solidifies. The solid is collected, then recrystallized from acetone/water, then from methanol to give the title compound, mp>300°; MS (m/e) 485, 463, 439 and 392; IR (mineral oil) 1685, 1598, 1582, 1493, 1235 and 1221 cm$^{-1}$; NMR (CDCl$_3$) 8.02, 7.57, 7.43, 7.26, 5.41, 3.98, 3.68, 3.28, 2.57, 2.50, 2.04, 1.29 and 0.98 δ; CMR (CDCl$_3$) 203.9, 138.7, 135.8, 133.5, 129.0, 128.6, 128.5, 127.3, 60.5, 60.4, 60.1, 60.0, 27.8, 33.8, 30.1, 15.9, 15.6 and 15.5 δ.

EXAMPLE 74

[4-Oxo-4-phenylbutylidene]bisphosphonic acid P-P'-diethyl ester disodium salt (III)

(4-Oxo-4-phenylbutylidene)bisphosphonic acid tetraethyl ester (III, EXAMPLE 47, 2.10 g) and sodium iodide (2.06 g) are heated in methyl ethyl ketone (10 ml) at reflux for 16 hours. The reaction is cooled, filtered, and washed with acetone. The precipitate is then dissolved in water and reprecipitated with acetone. The solid is collected, washed with acetone and ether, then air dried to give the title compound, mp>300°; MS (m/e) 409, 387 and 363; IR (mineral oil) 3394, 1683, 1598, 1581, 1450 and 1250 cm$^{-1}$; NMR (D$_2$O) 8.05, 7.69, 7.57, 3.93, 3.45, 2.16 and 1.22 δ.

EXAMPLE 75

(4-Oxo-3,4-diphenylbutylidene)bisphosphonic acid disodium salt hydrate (III)

(4-Oxo-3,4-diphenylbutylidene)bisphosphonic acid tetraethyl ester (Ill, EXAMPLE 11, 3.22 g) is heated in hydrochloric acid (concentrated, 16 ml) at reflux for 36 hours. The reaction is concentrated under reduced pressure, then concentrated under reduced pressure twice from toluene. A portion of the residue (1.39 g) is dissolved in methanol (7.2 ml) then treated with a solution of sodium hydroxide (290 mg) in methanol (3.5 ml). The reaction is stirred for 30 min then filtered. The precipitate is dissolved in water (4.1 ml), filtered through celite, then reprecipitated with acetone to give the title compound, mp>300°; MS (m/e) 429, 407, 389, 385, 365 and 105; IR (mineral oil) 1670, 1598, 1580 and 1217 cm$^{-1}$; NMR (D$_2$O) 8.07, 7.6–7.3, 5.4, 2.6, 2.4 and 1.8 δ.

EXAMPLE 76

(4-Cyano-3-(2-pyridinyl)butylidene)bisphosphonic acid (III)

[3-Cyano-3-(2-pyridinyl)propylidene]bisphosphonic acid tetraethyl ester (III, EXAMPLE 19, 5.460 g) and bromotrimethyl silane (7.8 ml) are stirred in chloroform (25 ml) at 500 for 6 hours, then concentrated under reduced pressure. The resulting oil is slurried in ethyl acetate/water and filtered, giving crude product (3.5 g). The pink powder resisted attempts at recrystallization, but the color could be removed. The sample is suspended in water (50 ml), then heated on the steam bath for 30 min, cooled and filtered. The sample is washed with ether and acetone, then air dried and finally dried in the vacuum oven to give the title compound, MS (m/e) 307, 221,177 and 118; IR (mineral oil) 2245, 1627, 1540 and 1340 cm$^{-1}$; NMR (CDCl$_3$) 8.52, 7.91, 7.61, 7.44, 2.40 and 1.96 δ.

EXAMPLE 77

[2-(1,2,3,4-Tetrahydro-1-oxo-2-naphtalenylethylidene]- bisphosphonic acid disodium salt (V)

(3-Benzoyl-1,5-pentanediylidene)tetrakisphosphonic acid octaethyl ester, 3.14 g) in chloroform (25 ml) is treated with bromotrimethyl silane (5.5 ml) and stirred at 40° for 5 hours, then diluted with ethyl acetate and water. The water layer is separated, and freeze dried. The acid is dissolved in methanol and treated with a sodium methoxide solution (25%, 3.0 g). The precipitate is collected, washed with ether, then dried in the vacuum oven to a constant weight to give the title compound, MS (m/e) 379, 378, 357, 335 and 317; IR (mineral oil) 1680, 1600, 1226 and 1002 cm$^{-1}$; NMR (D$_2$O) 7.91, 7.59, 7.37, 3.05, 2.36 and 1.8 δ; CMR (D$_2$O) 204, 145, 134, 131, 129, 126.6, 126.3, 46, 35, 27 and 25 δ.

EXAMPLE 78

[4-Oxo4-(2-thiazolylamino)-2-[(2-thiazolylamino) carbonyl]butylidene]bisphosphonic acid, tripotassium salt (III)

[4-Oxo-4-(2-thiazolylamino)-2-[(2-thiazolyl amino)-carbonyl]butylidene]bis phosphonic acid, tetraethyl ester (III, EXAMPLE 1, 1.325 g) and bromotrimethyl silane (1.50 ml) are heated to 40° in chloroform (5 ml) for 5 hours then concentrated under reduced pressure. The concentrate is treated with water and stirred overnight. A precipitate forms and is suspended in water (5 ml), treated with potassium hydroxide (250 mg) in water (5 ml). The reaction is stirred for 1 hour, filtered through celite, and freeze dried to give the title compound, MS (m/e) 533 (M+), 385, 347, 309; IR (mineral oil) 1681, 1567, 1492 and 1270 cm$^{-1}$; NMR (D$_2$O) 7.3, 6.8, 4.6, 3.39 and 2.86 δ.

EXAMPLE 79

(3-Methyl-4-oxo-4-phenylbutylidene)bisphosphonic acid disodium salt (III)

(3-Methyl-4-oxo4-phenylbutylidene)bisphosphonic acid tetraethyl ester (III, EXAMPLE 13, 2.0 g) and bromotrimethyl silane (3.5 ml) in chloroform (25 ml) are stirred at 50° for 19 hours then concentrated under reduced pressure. The concentrate is dissolved in ethyl acetate and water, shaken, then the water layer separated and freeze dried. The acid is dissolved in methanol (10 ml) and treated with a solution of sodium methoxide (25%, 2.0 g). A precipitate is collected, washed with methanol and ether, then dried in the vacuum oven to give the title compound, mp>300°; MS (m/e) 389, 367, 366, 345, 323 and 305; IR (mineral oil) 3064, 1679, 1597, 1225, 1161, 1076, 975 and 704 cm$^{-1}$; NMR (D$_2$O) 8.08, 7.70, 7.58, 4.15, 2.35, 2.14, 1.92 and 1.22 δ.

EXAMPLE 80

[4-Phenyl-3-butynylidene]bisphosphonic acid tetraethyl ester (X)

Phenylacetylene (IX, 4.4 g) is dissolved in THF (43 ml), cooled to −78°, and treated with lithium hexamethyldisilazide (1M in THF, 43 ml). The reaction is stirred for 30 min, then a solution of ethenylidenebisphosphonic acid tetraethyl ester (10.7 g) in THF (36 ml) is added and the reaction warmed to 22° for 1 hour. The reaction is quenched with water, extracted thrice with ethyl acetate. The organics were then washed with water, hydrochloric acid (10%), saturated sodium bicarbonate, and saline, dried with magnesium sulfate, and concentrated. The concentrate is purified by distillation, bp 0.1 195°-200°.

EXAMPLE 81

[3,4-Dioxo-4-phenylbutylidene]bisphosphonic acid tetraethyl ester (XI)

[4-Phenyl-3-butynylidene]bisphosphonic acid tetraethyl ester (X, EXAMPLE 80, 3.01 g) dissolved in methylene chloride (75 ml) and acetic acid (4.1 ml) is treated with benzyltriethylammonium chloride (0.42 g) and the solution is healed to reflux. A solution of potassium permanganate (4.83 g) in water (80 ml) is added and the solution is stirred at reflux for 4-6 hours and monitored by TLC. When complete, the mixture is cooled and acidified with hydrochloric acid (10%) and treated with sodium bisulfite to obtain a homogeneous solution. Separated and washed the aqueous layer twice with methylene chloride. Washed the combined organic layers with saturated sodium bicarbonate (3×), saline and dried with magnesium sulfate, then concentrated to an oil. The oil is chromatographed, eluting with ethyl acetate to give the title compound, MS (m/e) 434 (M+), 406, 389, 329, 301, 273, 245, 217, 133, 105; IR (solvent) 1720, 1673, 1597, 1580, 1450, 1392 and 1166 cm$^{-1}$; NMR (CDCl$_3$) 8.08, 7.64, 7.50, 4.19, 3.43), 3.34, 1.33 δ; CMR (CDCl$_3$) 197.3, 190.4, 134.4, 131.7, 130.3, 128.6, 62.7, 34.5, 30.7 and 16.1 δ.

EXAMPLES 82–89

Following the general procedure of EXAMPLES 80 and 81 and making non-critical variations but starting the appropriate starting material the following compounds are obtained:

82  [4-(3-Fluorophenyl)-3-butynylidene]bisphosphonic acid tetraethyl ester
83  [3,4-Dioxo4-(3-fluorophenyl)butylidene]bisphosphonic acid tetraethyl ester
84  [4-(3-Pyridyl)-3-butynylidene]bisphosphonic acid tetraethyl ester
85  [3,4-Dioxo4-(3-pyridyl)butylidene]bisphosphonic acid tetraethyl ester
86  [4-(3-Fluorophenyl)-butynylidene]-2,2'-bis[5,5-dimethyl-2,2'-dioxide 1,3,2-dioxaphosphorinane]
87  [3,4-Dioxo-4-(3-fluorophenyl)-butylidene]-2,2'-bis[5,5-dimethyl-2,2'-dioxide dioxaphosphorinane]
88  [4-(3-Pyridyl)-butynylidene]-2,2'-bis[5,5-dimethyl-2,2'-dioxide 1,3,2-dioxaphosphorinane]
89  [3,4-Dioxo-4-(3-pyridyl)-butylidene]-2,2'-bis[5,5-dimethyl-2,2'-dioxide 1,3,2-dioxaphosphorinane]

EXAMPLES 91–106

Following the general procedure of EXAMPLE 41 and making non-critical variations but starting with the appropriate starting materials the following compounds are obtained:

91  [4-Oxo-4-(3-fluorophenyl)-butylidene]-2,2'-bis[5,5-dimethyl-2,2'-dioxide 1,3,2-dioxaphosphorinane] (III) mp 201°-202°
92  [4-Oxo-4-(2-furanyl)-butylidene]-2,2'-bis[5,5-dimethyl-2,2'-dioxide 1,3,2-dioxaphosphorinane] (III) mp 247°-248°
93  [4-Oxo-4-(2-furanyl)-(3,3-dimethyl)-butylidene]-2,2'-bis [5,5-dimethyl-2,2'-dioxide 1,3,2-dioxaphosphorinane] (III) mp 169°-170°
94  [4-Oxo-4-(3-fluorophenyl)-(3,3-dimethyl)-butylidene]-2,2'-bis[5,5-dimethyl-2,2'-dioxide 1,3,2-dioxaphosphorinane] (III) mp 143°-144°
95  [4-Oxo-4-(4-fluorophenyl)-butylidene]-2,2'-bis[5,5-dimethyl-2,2'-dioxide 1,3,2-dioxaphosphorinane] (III) mp 174°-175°
96  [4-Oxo-4-(2-fluorophenyl)-butylidene]-2,2'-bis[5,5-dimethyl-2,2'-dioxide 1,3,2-dioxaphosphorinane] (III) mp 173°-174°
97  [4-Oxo-4-(3-pyridyl)-butylidene]-2,2'-bis[5,5-dimethyl-2,2'-dioxide 1,3,2-dioxaphosphorinane] (III) mp 183°-184°
98  [4-Oxo-4-(2,5-difluorophenyl)-butylidene]-2,2'-bis[5,5-dimethyl-2,2'-dioxide 1,3,2-dioxaphosphorinane] (III) mp 180°-181°

99 [4-Oxo-4-(2,6-difluorophenyl)-butylidene]-2,2'-bis[5,5-dimethyl-2,2'-dioxide 1,3,2-dioxaphosphorinane] (III) mp 192°–193°

100 [4-Oxo-4-(4-trifluoromethylphenyl)-butylidene]-2,2'-bis[5,5-dimethyl-2,2'-dioxide 1,3,2-dioxaphosphorinane] (III) mp 196°–187°

101 [4-Oxo-4-(3-trifluoromethylphenyl)-butylidene]-2,2'-bis [5,5-dimethyl-2,2'-dioxide 1,3,2-dioxaphosphorinane] (III) mp 174°–175°

102 [4-Oxo4-(2-trifluoromethylphenyl)-butylidene]-2,2'-bis[5,5-dimethyl-2,2'-dioxide 1,3,2-dioxaphosphorinane] (III) mp 90°–91°

103 [4-Oxo-4-(2,4-difluorophenyl)-butylidene]-2,2'-bis[5,5-dimethyl-2,2'-dioxide 1,3,2-dioxaphosphorinane] (III) mp 167°–168°

104 [4-Oxo-4-(3-methoxyphenyl)-butylidene]-2,2'-bis[5,5-dimethyl-2,2'-dioxide 1,3,2-dioxaphosphorinane] (III) mp 160°–161°

105 [4-Oxo-4-(2,3-difluorophenyl)-butylidene]-2,2'-bis[5,5-dimethyl-2,2'-dioxide 1,3,2-dioxaphosphorinane] (III) mp 186°–187°

106 (3-methoxy-4-oxo-4-phenyl)-butylidene]-2,2'-bis[5,5-dimethyl-2,2'-dioxide 1,3,2-dioxaphosphorinane] (III) mp 135°–136°

CHART A $CH_2=C[PO-(OR_1)_2]_2$     (I)

+

$R_2-X-(CW)_{m1}-CR_3R_4-H$     (II)

↓

$R_2-X-(CW)_{m1}-CR_3R_4-CH_2-CM[PO-(OR_1)_2]_2$     (III)

CHART B $CH_2=C[PO-(OR_1)_2]_2$     (I)

+

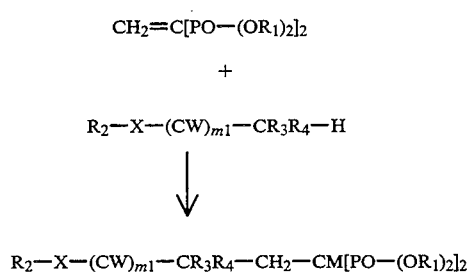 (IV)

↓

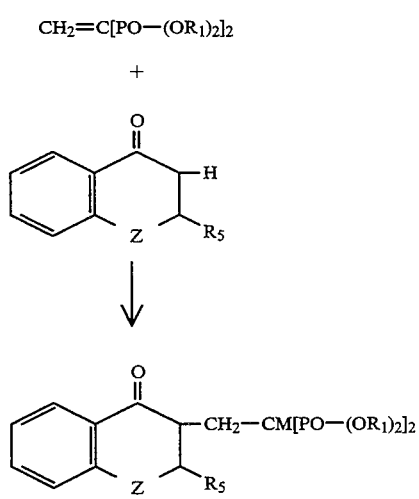 (V)

CHART C $CH_2=C[PO-(OR_1)_2]_2$     (I)

+

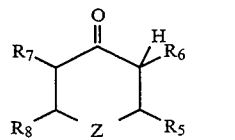 (VI)

↓

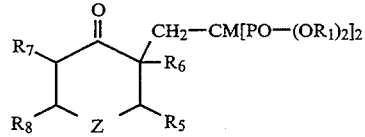

CHART D $CH_2=C[PO-(OR_1)_2]_2$     (I)

+

$R_2-C\equiv C-H$     (IX)

↓

$R_2-C\equiv C-CH_2CM[PO-(OR_1)_2]_2$     (X)

↓

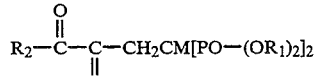 (XI)

I claim:

1. Acyclic bisphosphonates of the formula (III)

$R_2-X-(CW_1)_{m1}-CR_3R_4-CH_2-CM[PO-(OR_1)_2]_2$     (III)

where (I) $m_1$ is 0 or 1;

(II) M is —H, —Cl or —CH$_3$;

(III) $R_1$ are the same or different and are selected from the group consisting of
(A) —H,
(B) $C_1$–$C_6$ alkyl,
(C) —CH$_2$—φ;

(IV) $R_2$ is
(A) — optionally substituted with 1 or 2 —φ or with 1 thru 3
(1) —F,
(2) —Cl,
(3) —Br,
(4) —I,
(5) —NO$_2$,
(6) —CN,
(7) —CF$_3$,
(8) $C_1$–$C_{10}$ alkyl,
(9) $C_3$–$C_7$ cycloalkyl,
(10) —OH,
(11) $C_1$–$C_4$ alkoxy,
(12) —SH,
(13) —NH$_2$,
(14) —O—CO—$R_{2-1}$ where $R_{2-1}$ is (a) $C_1-C_{10}$ alkyl,
(b) $C_3-C_7$ cycloalkyl,
(15) $-(CH_2)_{n1}-COO-R_{2-2}$ where $n_1$ is 1 thru 3 and $R_{2-2}$ is
  (a) $-H$,
  (b) $C_1-C_6$ alkyl,
  (c) $-CH_2-\phi$,
  (d) $-N-CO-R_{2-3}$ where $R_{2-3}$ is
    (i) $C_1-C_{10}$ alkyl,
    (ii) $C_3-C_7$ cycloalkyl,
  (e) $-(CH_2)_{n4}-COO-R_{2-9}$ where $n_4$ is 1 thru 3 and $R_{2-9}$ is
    (i) $-H$,
    (ii) $C_1-C_6$ alkyl,
    (iii) $-\phi$,
(16) $-O-S(O)_2-R_{2-4}$ where $R_{2-4}$ is
  (a) $C_1-C_{10}$ alkyl,
  (b) $-\phi$ optionally substituted with 1 thru 3
    (i) $-F$,
    (ii) $-Cl$,
    (iii) $-Br$,
    (iv) $-I$,
    (v) $-NO_2$,
    (vi) $-CN$,
    (vii) $-CF_3$,
    (viii) $C_1-C_{10}$ alkyl,
    (ix) $-OH$,
    (x) $C_1-C_4$ alkoxy,
    (xi) $-O-\phi$,
    (xii) $C_1-C_4$ alkylthio,
    (xiii) $-NH-CO-R_{2-3}$ where $R_{2-3}$ is as defined above,
(17) $-N(R_{2-5})(R_{2-6})$ where $R_{2-5}$ and $R_{2-6}$ are the same or different and are
  (a) $-H$,
  (b) $C_1-C_6$ alkyl,
  (c) $C_3-C_7$ cycloalkyl,
  (d) $-\phi$,
(18) $-N(R_{2-7})-CO-R_{2-3}$ where $R_{2-7}$ is
  (a) $-H$,
  (b) $C_1-C_6$ alkyl,
  (c) $C_3-C_7$ cycloalkyl,
  (d) $-\phi$, and where $R_{2-3}$ is as defined above,
(19) $-N(R_{2-7})-CO-O-R_{2-8}$ where $R_{2-8}$ is
  (a) $-H$,
  (b) $C_1-C_6$ alkyl,
  (c) $-\phi$ and
  (d) $-CH_2-\phi$, and where $R_{2-7}$ is as defined above,
(20) $-N(R_{2-7})-CO-N(R_{2-5})(R_{2-6})$ where $R_{2-5}$, $R_{2-6}$ and $R_{2-7}$ are as defined above,
(21) $-N(R_{2-7})-SO_2-R_{2-4}$ where $R_{2-4}$ and $R_{2-7}$ are as defined above,
(B) 1- and 2-naphthalyl optionally substituted with 1 or 2 $-\phi$, or with 1 thru 3
  (1) $-F$,
  (2) $-Cl$,
  (3) $-Br$,
  (4) $-I$,
  (5) $-CN$,
  (6) $-CF_3$,
  (7) $C_1-C_{10}$ alkyl,
  (8) $C_3-C_7$ cycloalkyl,
  (9) $-OH$,
  (10) $-SH$,
  (11) $-NH_2$,
  (12) $-O-CO-R_{2-1}$ where $R_{2-1}$ is as defined above,
  (13) $-O-S(O)_2-R_{2-4}$ where $R_{2-4}$ is as defined above,
  (14) $-N(R_{2-5})(R_{2-6})$ where $R_{2-5}$ and $R_{2-6}$ are as defined above,
  (15) $-N(R_{2-7})-CO-R_{2-3}$ where $R_{2-3}$ and $R_{2-7}$ are as defined above,
  (16) $-N(R_{2-7})-CO-O-R_{2-8}$ where $R_{2-7}$ and $R_{2-8}$ are as defined above,
(VA) ($R_3/R_4$-I) $R_3$ and $R_4$ together with the attached carbon atom form a cycloalkyl ring of 3 thru 7 carbon atoms,
(VB) ($R_3/R_4$-II) $R_3$ is $-H$ and $R_4$ is
  (A) $-H$,
  (B) $R_{2-4}$,
  (C) $-CO-O-R_{2-2}$,
  (D) $-CO-R_2$,
  (E) $-CN$,
  (F) $-CO-NH-R_2$,
  (G) $-NH-CO-R_{2-3}$, and
(VC) ($R_3/R_4$-III) $R_3$ is $-H$ and $R_4$ is $-F$, $-Cl$, $-Br$ or $-I$,
(VD) ($R_3/R_4$-IV) $R_3$ and $R_4$ are the same or different and are $C_1-C_{10}$ alkyl;
(VIA) ($W_1$-I) $W_x$ is
  (A) $=O$,
  (B) $=S$,
  (C) $=N-N(R_{2-7})_2$ where $R_{2-7}$ is as defined above,
(VIB) ($W_1$-II) $W_1$ is $W_{1-1}$:$W_{1-2}$ where $W_{1-1}$ and $W_{1-2}$ are the same and are $C_1-C_4$ alkoxy,
(VIC) ($W_1$-IV) $W_1$ is $-H$:$W_{1-5}$ where $W_{1-5}$ is
  (A) $-OH$,
  (B) $-SH$,
  (C) $-NH_2$,
  (D) $-S-W_{1-6}$ where $W_{1-6}$ is $C_1-C_4$ alkyl,
  (E) $-O-CO-R_{2-1}$ where $R_{211}$ is as defined above,
  (F) $-N(R_{2-5})(R_{2-6})$ where $R_{2-5}$ and $R_{2-6}$ are as defined above,
  (G) $-N(R_{2-7})-CO-R_{2-3}$ where $R_{2-3}$ and $R_{2-7}$ are as defined above,
  (H) $-N(R_{2-7})-CO-O-R_{2-8}$ where $R_{2-7}$ and $R_{2-8}$ are as defined above;
(VII) X is $-(CH_2)_{n2}-$ or $-(CH=CH)_{n3}-$ where $n_2$ is 0 thru 5 and $n_3$ is 0 thru 2, with the proviso that when $R_4$ is $-R_{2-4}$, $m_1$ is 1, or pharmaceutically acceptable salts thereof.

2. An acyclic bisphosphonate of formula (III) according to claim 1 which is selected from the group consisting of:

(3,3-dibenzoylpropylidene)bisphosphonic acid tetraethyl ester,
[4-(4-hydroxphenyl)-4-oxo-3-phenylbutylidene]bisphosphonic acid tetraethyl ester,
(4-oxo-3,4-diphenylbutylidene)bisphosphonic acid tetraethyl ester,
(3-benzoyl-4-ethoxy-4-oxobutylidene)bisphosphonic acid tetraethyl ester,
(3-methyl-4-oxo-4-phenylbutylidene)bisphosphonic acid tetraethyl ester,
[4-(4-bromophenyl)-4-oxo-3-phenylbutylidene]bisphosphonic acid tetraethyl ester,
[4-oxo-4-(4-biphenyl)-3-phenylbutylidene]bisphosphonic acid tetraethyl ester,
[4-(4-methoxyphenyl)-4-oxo-3-(phenylbutylidene]bisphosphonic acid tetraethyl ester,
α-[2,2-bis(ethoxyphosphinyl)ethyl]-benzene acetic acid methyl ester, (3-cyano-3-phenylpropylidene)bisphosphonic acid tetraethyl ester,
[3-cyano-3-(2-naphthyl)propylidene]bisphosphonic acid tetraethyl ester,
[1-naphthyl-4-nitrilobutylidene]bisphosphonic acid tetraethyl ester,
[3-carbomethoxy-3-(1-naphthenyl)-propylidine]bisphosphonic acid tetraethyl ester,
[3-methoxy-4-oxo-4-phenylbutylidene]bisphosphonic acid tetraethyl ester,
[4-oxo-4-phenyl-3-phenylthio-butylidene]bisphosphonic acid tetraethyl ester,
[3-benzoylamino-4-oxo-4-phenylbutylidene]bisphosphonic acid tetraethyl ester,
[3-t-butoxycarbonylamino-4-oxo-4-phenyl-butylidene]bisphosphonic acid tetraethyl ester,
[4-(3'-fluorophenyl)-4-oxo-butylidene]bisphosphonic acid tetraethyl ester,
[4-(4'-ethoxycarbonylaminophenyl)-4-oxobutylidene]bisphosphonic acid tetraethyl ester,
[4-(4'-acetamidophenyl)-4-oxo-butylidene]bisphosphonic acid tetraethyl ester,
[1-methyl-4-oxo-4-phenylbutylidene]bisphosphonic acid tetraethyl ester,
[4-(4'-hydroxyphenyl)-4-oxo-butylidene]bisphosphonic acid tetraethyl ester,
[4-(2'-hydroxyphenyl)-4-oxo-butylidene]bisphosphonic acid tetraethyl ester,
(4-oxo-4-phenylbutylidene)bisphosphonic acid tetraethyl ester,
[4-(4'-methylphenyl)-4-oxo-butylidene]bisphosphonic acid tetraethyl ester,
[4-(4'-methoxyphenyl)-4-oxo-butylidene]bisphosphonic acid tetraethyl ester,
[4-oxo-4-(2',3',4'-trichlorophenyl)-butylidene]bisphosphonic acid tetraethyl ester,
[4-(3',5'-difluorophenyl)-4-oxo-butylidene]bisphosphonic acid tetraethyl ester,
[4-(4'-chlorophenyl)-4-oxo-butylidene]bisphosphonic acid tetraethyl ester,
[3,3-dimethyl-4-oxo-4-phenylbutylidene]bisphosphonic acid tetraethyl ester,
[4-(3',4'-dichlorophenyl)-4-oxo-butylidene]bisphosphonic acid tetraethyl ester,
[1-chloro-4-oxo-4-phenylbutylidene]bisphosphonic acid tetraethyl ester,
[4-oxo-6-phenyl-hex-5-en-ylidene]bisphosphonic acid tetraethyl ester,
[4-(2'-benzamidophenyl)-4-oxo-butylidenelbisphosphonic acid tetraethyl ester,
[4-(3'-ethoxycarbonylaminophenyl)-4-oxo-butylidene]bisphosphonic acid tetraethyl ester,
[4-(4'-(4-chlorobenzamido)phenyl)-4-oxo-butylidene]bisphosphonic acid tetraethyl ester,
[4-(3'-(4-nitrobenzamido)phenyl)-4-oxo-butylidene]-bisphosphonic acid tetraethyl ester,
[4-(4'-benzamidophenyl)-4-oxo-butylidene]bisphosphonic acid tetraethyl ester,
[4-hydroxy-4-phenylbutylidene]bisphosphonic acid tetraethyl ester,
[4-hydroxy-3,4-diphenylbutylidene]bisphosphonic acid tetraethyl ester,
[1,3,3-trichloro-4-oxo-4-phenylbutylidene]bisphosphonic acid tetraethyl ester.

3. An acyclic bisphosphonate of formula (III) according to claim 1 where $m_1$ is 1.

4. An acyclic bisphosphonate of formula (III) according to claim 1 where $R_1$ is $C_1$–$C_2$ alkyl or —H or a pharmaceutically acceptable salt thereof.

5. An acyclic bisphosphonate of formula (III) according to claim 1 where $R_3$ is —H.

6. An acyclic bisphosphonate of formula (III) according to claim 1 where $R_4$ is —H, $R_{2-4}$, —CO—O—$R_{2-8}$, —CO—$R_2$, —CN and —CO—NH—$R_2$.

7. An acyclic bisphosphonate of formula (III) according to claim 1 where $W_1$ is =O.

8. An acyclic bisphosphonate of formula (Ill) according to claim 1 where $n_2$ and $n_3$ are 0.

* * * * *